(12) United States Patent
Franjic et al.

(10) Patent No.: US 7,630,418 B2
(45) Date of Patent: Dec. 8, 2009

(54) LASER SYSTEM FOR GENERATION OF HIGH-POWER SUB-NANOSECOND PULSES WITH CONTROLLABLE WAVELENGTH IN 2-15 μM REGION

(76) Inventors: Kresimir Franjic, 1545 Bathurst St. Apt #404, Toronto (CA) M5P 3H6; Darren Kraemer, 33 Himount Drive, Toronto (CA) M2K 1X3; Michael L. Cowan, 117 Gerrard St. E. Apr. #903, Toronto (CA) M5B 2L4; Renzhong Hua, 240 Wellesley St., East, Apt. #821, Toronto (CA) M4X 1G5; R. J. Dwayne Miller, 21 Elmwood Avenue, Port Credit (CA) L5G 3J6

( * ) Notice: Subject to any disclaimer, the term of this patent is extended or adjusted under 35 U.S.C. 154(b) by 115 days.

(21) Appl. No.: 11/328,462

(22) Filed: Jan. 10, 2006

(65) Prior Publication Data

US 2006/0153254 A1   Jul. 13, 2006

Related U.S. Application Data

(60) Provisional application No. 60/642,113, filed on Jan. 10, 2005.

(51) Int. Cl.
*H01S 3/10* (2006.01)
(52) U.S. Cl. ............................ 372/21; 372/4
(58) Field of Classification Search ............... 372/21, 372/22; 359/327, 330
See application file for complete search history.

(56) References Cited

U.S. PATENT DOCUMENTS 4,917,083 A * 4/1990 Harrington et al. ............. 606/15

(Continued)

FOREIGN PATENT DOCUMENTS

WO       WO 97/26830       7/1997

(Continued)

OTHER PUBLICATIONS

Deak et al., "High-power picosecond mid-infrared optical parametric amplifier for infrared Raman spectroscopy", Dec. 1, 1997, Optical Society of America, Optics Letters, vol. 22, No. 23, 1796-1797.*

(Continued)

*Primary Examiner*—Minsun Harvey
*Assistant Examiner*—Joshua King
(74) *Attorney, Agent, or Firm*—Lynn C. Schumacher; Hill & Schumacher

(57) ABSTRACT

A laser system capable of efficient production of high energy sub-nanosecond pulses in the 2-15 μm spectral region is disclosed. Diode pumped solid state lasers are used as pump sources. The system design is simple, reliable and compact allowing for easy integration. The laser system includes a combination of compact solid-state ~1 micron laser sources, producing high power picosecond pulses, with optical parametric amplification and a quasi-continuous wave laser for seeding the amplification process that enables the efficient conversion of the high power ~1 micron laser radiation to tuneable mid-infrared sub-ns pulses. New parametric processes are presented for achieving high gains in bulk nonlinear crystals. Furthermore, a method of exceeding the fundamental conversion efficiency limit of direct three wave mixing is presented. The compact and robust nature of this novel laser system opens up the use of high power and high peak power mid-infrared laser pulses to a wide variety of important medical and dental applications.

46 Claims, 11 Drawing Sheets

U.S. PATENT DOCUMENTS

| | | | | |
|---|---|---|---|---|
| 5,943,161 | A * | 8/1999 | Shinozaki et al. | 359/330 |
| 6,081,369 | A * | 6/2000 | Waarts et al. | 359/341.33 |
| 6,198,568 | B1 * | 3/2001 | Galvanauskas et al. | 359/332 |
| 6,208,458 | B1 * | 3/2001 | Galvanauskas et al. | 359/345 |
| 6,301,273 | B1 * | 10/2001 | Sanders et al. | 372/6 |
| 6,344,921 | B1 * | 2/2002 | Galvanauskas et al. | 359/332 |
| 6,919,985 | B2 * | 7/2005 | Furukawa et al. | 359/326 |
| 7,388,709 | B1 * | 6/2008 | Vachss et al. | 359/326 |
| 2002/0057757 | A1 | 5/2002 | Khoury | 378/21 |
| 2003/0112494 | A1 * | 6/2003 | Barty et al. | 359/330 |
| 2006/0050749 | A1 * | 3/2006 | Setzler | 372/22 |
| 2006/0245461 | A1 * | 11/2006 | Islam | 372/75 |

FOREIGN PATENT DOCUMENTS

| | | |
|---|---|---|
| WO | WO 01/51243 | 7/2001 |

OTHER PUBLICATIONS

Yao et al., "Pump-tuning optical parametric oscillation and sum-frequency mixing with KTP pumped by a Ti:sapphire laser", Jun. 1, 2001, Optics Communications, 192, 407-416.*

Finsterbusch et al., "Tunable, narrow-band picosecond radiation in the mid-infrared by difference frequency mixing in GaSe and CdSe", 2004, Applied Physics B, 79, 457-462.*

Baxter et al., "A pulsed optical parametric oscillator, based on periodically poled lithium niobate (PPLN), for high-resolution spectroscopy", 1998, Applied Physics B, 67, 753-756.*

Wang et al., "Tunable femtosecond optical parametric amplifier with weak CW seeding", May 21, 2004, Optical Communications, 239, 397-401.*

Kaindl, Robert A., Wurm, Matthias, Reimann, Klaus, Hamm, Peter, Weiner, Andrew M., Woerner, Michael. *Generation, shaping, and characterization of intense femtosecond pulses tubable from 3 to 20 $\mu m$*. J. Opt. Soc. Am. B, vol. 17, No. 12, pp. 2086-2094. Dec. 2000.

Finsterbusch, K., Urschel, R., Zacharias, H. *Tunable, high-powered, narrow-band picosecond IR radiation by optical parametric amplification in KTP*. Appl. Phys. B 74, pp. 319-322. 2002.

Finsterbusch, K., Bayer, A., Zacharias, H. *Tunable, narrow-band picosecond radiation in the mid-infrared by difference frequency mixing in GaSe and CdSe*. Appl. Phys. B 79, pp. 457-462. 2004.

Rotermund, F., Petrov, V., Noack, F., Pasiskevicius, V., Hellström, J., Laurell, F., Hundenmark, H., Adel, P., Fallnich, C. *Compact all-diode-pumped femtosecond laser source based on chirped pulse optical parametric amplification in periodically poled $KTiOPO_4$*. Electronics Letters, vol. 38, No. 12, pp. 581-583. Jun. 6, 2002.

Fradkin-Kashi, K., Arie, A., Urenski, P., Rosenman, G. *Mid-infrared difference-frequency generation in periodically poled $KtiOAsO_4$ and application to gas sensing*. Optics Letters, vol. 25, No. 10, pp. 743-745. May 15, 2000.

Matsuura, Yuji, Miyagi, Mitsunobu. *Er: YAG, CO, and $CO_2$ laser delivery by ZnS-coated AG hollow waveguides*. Applied Optics, vol. 32, No. 33, pp. 6598-6601. Nov. 20, 1993.

Yamashita, Shinji, Hotate, Kazuo, Ito, Masataka. *Polarization Properties of a Reflective Fiber Amplifier Employing a Circulator and a Faraday Rotator Mirror*. Journal of Lightwave Technology, vol. 14, No. 3, pp. 385-390. Mar. 1996.

Rusu, Matei, Herda, Robert, Okhotnikov, Oleg G. *Passively synchronized two-color mode-locked fiber system based on master-slave lasers geometry*. Optics Express, vol. 12, No. 20, pp. 4719-4724. Oct. 4, 2004.

* cited by examiner

LASER SYSTEM FOR GENERATION OF HIGH-POWER SUB-NANOSECOND PULSES WITH CONTROLLABLE WAVELENGTH IN 2-15 µM REGION

CROSS REFERENCE TO RELATED U.S PATENT APPLICATION

This patent application relates to U.S. provisional patent application Ser. No. 60/642,113 filed on Jan. 10, 2005 entitled LASER SYSTEM FOR HIGHLY EFFICIENT GENERATION OF HIGH-POWER SUB-NANOSECOND NARROWBAND PULSES WITH CONTROLABLE WAVELENGTHS IN 2-15 µm REGION, filed in English, which is incorporated herein by reference in its entirety.

FIELD OF THE INVENTION

The present invention relates to a laser method for efficient generation of high-power sub-nanosecond (ns) pulses with controllable wavelengths in the mid infrared (IR), 2-15 µm spectral region. These pulses have particular importance to applications in the medical and dental fields for impulsive heat deposition (IHD) under inertial confinement for minimally invasive surgery and dental procedures. This invention constitutes a compact and robust solution to generating the prerequisite pulse properties with respect to wavelength and time profiles to achieve minimal heat transfer and collateral damage to adjacent materials. This invention promises to open up new fields in tissue removal and other material processing applications with unprecedented minimization of collateral damage to the surrounding material.

BACKGROUND OF THE INVENTION

Amplified sub-nanosecond laser pulses in the mid-IR spectral range (2-15 µm) are increasingly important for new scientific, technological and medical applications. These wavelengths are useful because they are resonant with the vibrational transitions that provide fingerprints that are highly specific to a particular molecule or material. This unique property of absorption in the infrared spectral region imparts important novel properties to high peak power and average power mid-IR lasers. Tuning to match specific vibrations enables the selective excitation of materials as means to selectively process and shape the material through ablation.

Utilization of this phenomena has led to recent advances in the laser processing of materials, which is based on a new understanding of the ablation process and the dynamics of transduction of vibrational energy into heat. This novel method of laser ablation, as detailed in U.S. patent application Ser. No. 11/321,057, filed Dec. 30, 2005, is able to achieve efficient material ablation with the minimum of collateral damage through either ion formation or thermal accumulation. This is accomplished by impulsive heat deposition (IHD), a novel method that combines both thermally and photomechanically driven ablation mechanisms, in which most of the absorbed energy remains in the ablated material [1]. The laser energy is coupled directly to the mechanical degrees of freedom that lead to ablation with optimal efficiency, which is key to minimizing collateral damage. Stated most succinctly, if the material can be energized and this energy is thermalized into heat faster than the material can expand, all the energy becomes stored locally.

As soon as the material or one constituent of the material (e.g. micropools of water in cells) has its temperature raised approximately two times its equilibrium phase transition, the material will undergo an explosive phase transition driven by homogeneous nucleation unique to inertial confinement. The ensuing volume changes and thermal expansion lead to material ablation faster than the speed of sound and most of the deposited laser energy is released as kinetic energy in the ablation process. IHD only occurs when the exciting laser pulses have pulse durations shorter than the expansion time of the irradiated volume, which is on the sub-ns time scale for resonant mid-IR pulses. The challenge for practical application of this technology is to develop robust, compact laser systems with the correct wavelength and pulse durations to meet this condition.

Of prime importance is the generation of high peak power IR that is resonant with specific vibrational modes of water. The vibrational modes of water (OH stretch, OH bend and combinations) are the key to selectively deposit energy for laser cutting of biological materials. The lifetime of these vibrations are less than 200 fs so the laser deposited energy will essentially track the laser pulse time profile. In addition, the absorption is so strong that 90% of the IR tuned to the OH vibration is absorbed in a thickness of less than 1 µm. However, many other molecular vibrations are sufficiently short lived to satisfy the condition of IHD and most materials have a sufficiently high number density of at least one vibrational mode to ensure strong localization of the laser deposited energy. Mid-IR laser sources with the necessary pulse characteristics required for this application of IHD are currently too complex and costly to be of practical utility.

High energy, sub-ns mid-IR pulses were first generated by Free Electron Lasers. These devices are confined to large facilities and thus the expense and size of such systems limits their practical use. The lack of compact and simple laser sources in the mid-IR wavelength regions is due to the scarce choice of resonant laser gain media in this wavelength range. The few gain materials that are capable of resonant gain in the mid-IR, such as Er:YAG, Cr:YAG, etc. are either unsuitable for high power operation, or lack the necessary bandwidth to make picosecond (ps) pulses.

A number of methods using non-resonant nonlinear processes have been previously developed for generating sub-ns pulses in the mid-IR. However, until the invention disclosed herein all have suffered from drawbacks and are not suited for practical medical applications due to either their complexity or low efficiency and power.

There are at least three methods that involve the use of amplified Ti:Sapphire femtosecond pulses to produce broadband sub-ns mid-IR pulses. The first is continuum seeded difference frequency mixing, in which ultrafast mid-IR pulses are generated in a multi step process where short pulses at wavelengths between 1-2 µm are produced by an OPA, and the resulting signal and idler beams are then combined to produce pulses in 2-15 µm spectral region by difference frequency generation (DFG) [3, 4]. The second is the technique of an OPA with narrowband near-IR seed pulses [5]. The third reaches mid-IR wavelengths using an Optical Parametric Oscillators (OPO) pumped by Ti:Sapphire femtosecond pulses [2]. However the direct output of OPO's cannot produce the high energy picosecond pulses that are needed for these applications without subsequent amplification in an optical parametric amplifier (OPA).

All of these methods use Ti:Sapphire femtosecond pumps, which results in expensive, large, and complex systems which are not suitable as robust tools for use outside of the research environment. They involve no fewer than 6 individually complex subsystems requiring 10-µm sensitive alignment precision of at least 100 optomechanical mounts. The cost of these subsystems, and the prospect of keeping them all aligned to the required precision has prohibited the entry of such technology into general practice in all but a few applications. These Ti:Sapphire based schemes are also energetically inefficient, leading to relatively low output powers at mid-IR wavelengths.

High power mid-IR pulses can also be derived from picosecond solid state IR sources. In many such systems, the mid-IR seed pulses originate from optical parametric generation (OPG), which has a number of problems, including angular dispersion, low conversion efficiency and short coherence lengths [6]. The simplest method to date capable of generating tunable sub-ns picosecond mid-IR pulses requires a solid state laser oscillator, an OPO based on periodically poled crystals (for generating tunable near-IR picosecond seed pulses from the oscillator pulses) and a regenerative amplifier to amplify the oscillator pulses to high energy pump pulses [7]. Subsequent mixing to longer wavelengths was demonstrated in such a system with the use of additional OPA stages [8]. This method also suffers from high complexity due to the large number of complicated sub-systems required.

The method of seeding an OPA with ultrafast pulses that have been chirped for longer pulse durations is referred to as Optical Parametric Chirped Pulse Amplification (OPCPA). Such systems pumped by narrowband 1 µm pulses and seeded with chirped ultrashort Er:fibre 1.5 µm pulses, [9] are capable of generating broadband sub-ns pulses in the mid-IR. However, these previously implemented OPCPA systems also require many complicated and expensive sub-systems, limiting their use in medical and dental applications.

Despite the numerous attempts and the numerous methods available, no practical devices have been proposed or realized that can efficiently produce sub-ns pulses with repetition rates (<1 MHz), capable of supporting high pulse energy (>10 µJ) and spectrums in the wavelength region of 2-15 µm that are sufficiently low cost and robust for application in the medical and dental fields. We present a solution to this problem using OPA techniques to develop a novel method and laser apparatus capable of efficient generation of high-power sub-nanosecond pulses with controllable wavelengths in the 2 to 15 µm spectral region with a compact and robust design.

SUMMARY OF THE INVENTION

This invention provides a highly compact tuneable laser system that is capable of generating mid-IR pulses with sub-ns pulse durations and pulse energies greater than 10 µJ. The pulse generation is based on three wave mixing in one or more bulk nonlinear crystals acting as an optical parametric amplifier (OPA). The OPA is pumped at a wavelength between 1.0 and 1.1 µm by a pulsed laser with a pulse duration of 1 to 1000 ps. When seeded with wavelengths between 1 and 2 µm, the OPA is capable of generating idler pulses of 2 to 15 µm. The maximum power output of the device is limited only by the pump laser power and the aperture of the nonlinear crystals.

In one aspect of the invention there is provided a method of producing high power picosecond (ps) mid-infrared (IR) laser pulses having a wavelength $\lambda_3$ between 2 and 15 µm, comprising the steps of:

a) producing high energy pump pulses with a wavelength $\lambda_1$, between about 1 and about 1.1 µm, a pulse duration between about 1 and about 1000 ps, and an energy larger than about 10 µJ;

b) producing a low power continuous wave (CW) laser beam, having a power in a range between about 1 to about 100 mW, with a wavelength $\lambda_2$, satisfying a relation $1/\lambda_2=1/\lambda_1-1/\lambda_3$ wherein said wavelength $\lambda_2$ is between about 1.19 to 2 µm;

c) directing, focusing and combining said pump pulses and said CW laser beam in such a way that they have substantial spatial overlap, and directing the combined pump pulses and OW laser beam into at least one optical parametric amplifier each having at least one bulk non-linear optical crystal, without said CW laser beam passing through a optical parametric oscillator before entering said optical parametric amplifier, with the peak intensity of the pump pulses sufficient such that high energy picosecond mid-IR pulses at wavelength $\lambda_3$ between 2 and 15 µm are produced through three wave mixing between said spatially overlapped pump pulses and CW laser beam in said at least one bulk non-linear optical crystal; and d) directing said high energy picosecond mid-IR pulses at wavelength $\lambda_3$ between 2 and 15 µm from an output of said at least one optical parametric amplifier to a desired location.

In another aspect of the present invention there is provided a laser system to produce high power broadband mid-infrared (IR) laser pulses having a wavelengths $\lambda_3$ lying between 2 and 15 µm, comprising:

a) a laser for producing high energy pump pulses with wavelength $\lambda_1$ between about 1.0 and about 1.1 µm, pulse duration between about 1 and about 1000 ps and high energy larger than about 10 µJ;

b) a low power laser for producing low power continuous wave (CW) laser beam having a power in a range between about 1 to about 100 mW, with a wavelength $\lambda_2$ satisfying a relation $1/\lambda_2=1/\lambda_1-1/\lambda_3$ wherein said wavelength $\lambda_2$ is between about 1.19 to about 2 µm;

c) at least one optical parametric amplifier, each having at least one bulk non-linear optical crystal;

d) means for directing, focusing and combining said high energy pump pulses and said CW laser beam in such a way that they have substantial spatial and temporal overlap, and directing said combined high energy pump pulses and CW laser beam into said at least one optical parametric amplifier, said at least one optical parametric amplifier having at least one bulk non-linear optical crystal, without an optical parametric oscillator being present between the CW laser beam and said optical parametric amplifier, with the peak intensity of the high energy pump pulses sufficient such that high energy broadband mid-IR pulses at wavelengths $\lambda_3$ between 2 and 15 µm are produced through three wave mixing between said spatially overlapped high energy pump pulses and CW laser beam in said at least one bulk non-linear crystal;

e) means for shaping the spectral and temporal profile of said high energy broadband mid-IR pulses either directly at said mid-IR wavelengths, or indirectly through the shaping of said CW laser beam before said at least one optical parametric amplifier; and f) means for transporting said high energy broadband mid-IR pulses at wavelengths $\lambda_3$ from an output of said at least one optical parametric amplifier to a desired location.

BRIEF DESCRIPTION OF THE DRAWINGS

The laser system produced according to the present invention will now be described, by way of example only, reference being made to the accompanying drawings, in which.

DETAILED DESCRIPTION OF THE INVENTION

Figure 1:
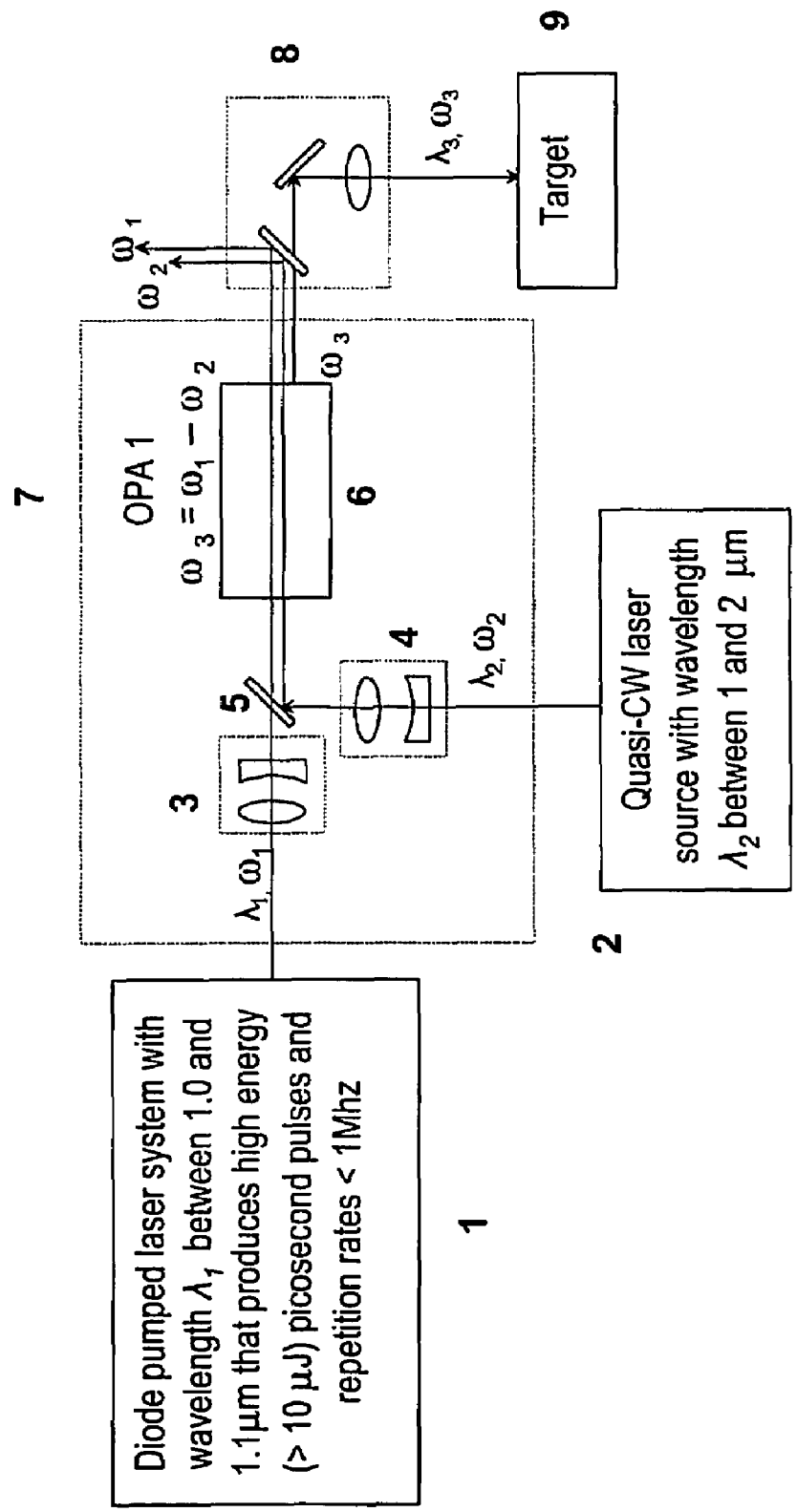
FIG. 1 is a schematic of the disclosed laser system for producing high power sub-nanosecond mid-IR pulses in 2-15 µm spectral range constructed in accordance with the present invention.

Disclosed herein is a novel practical method and laser apparatus for the generation of tuneable sub-ns optical pulses with high energies and wavelengths in the mid-IR (2-15 µm).

One aspect of this invention provides a way to efficiently convert the energy from high power and compact picosecond 1 µm laser sources to high power infrared picosecond pulses of longer wavelengths, by seeding with quasi-CW infrared laser radiation. Where quasi-CW is defined as continuous wave (CW) radiation or laser pulses not generated by a mode-locked laser resonator. Quasi-CW sources include gain-switched, Q-switched and amplitude modulated CW lasers. Seeding a high gain parametric amplifier with a quasi-CW laser results in the amplification of a temporal portion of the seed, resulting in a pulse with similar duration as the pump pulse. [10] Only periodically poled nonlinear materials were thought capable of generating the necessary optical parametric gain for the amplification of weak quasi-CW seeds to high power sub-ns pulses. However, these crystals are very costly to produce and can only be made with small apertures, limiting their maximum output power. In this novel implementation, we show how bulk non-linear crystals can be used to generate high power mid-IR pulses.

The various bulk nonlinear crystals that can be used in this system operate with different bandwidths and in different wavelength ranges depending on their phase matching conditions. The wavelength range around 3 µm is particularly important to laser ablation of biological tissue. This range contains a large peak in the absorption spectrum of water, due to the OH stretching vibrations. The teachings in this invention can be used to construct a novel apparatus, based on existing and widely available components, that is practical for applications that require high energy 3 µm sub-ns pulses. The bulk nonlinear crystal, potassium titanyl arsenate (KTA) is a suitable, inexpensive and robust material for parametric mixing at these wavelengths. In a number of configurations it has sufficient gain that high power mid-IR output pulses can be obtained from single bulk crystals, even when seeded with low power CW diodes. Conveniently, the seed wavelengths required to operate this apparatus at 3 µm coincide with the operating wavelengths of inexpensive robust low power telecommunications diodes around 1.6 µm. Available diodes have high stability and ideal spatial characteristics for seeding the OPA.

Practical use in the fields of clinical medicine and dentistry, requires that the apparatus contain a beam delivery system, such that the output of the laser can be conveniently transported to a region of interest. Suitable beam delivery can be accomplished by delivering the output pulses of the OPA to the desired location with a flexible waveguide capable of transmitting said pulse energy, peak power and wavelength without detrimental alteration of the pulses. Hollow core fiber waveguides designed for high power 3 µm pulses are well known to those skilled in the art. [11]

The apparatus, as described above can be constructed from simple and easily available components, including a compact 1 µm high power ps pump source, 1.6 µm low power seed source, at least one bulk nonlinear crystal, a beam delivery waveguide, minimal optical elements to combine and shape the seed and pump beams, and optical components to filter the OPA output and couple to the beam delivery waveguide. Construction of such an apparatus for long term stability of the alignment of the respective components can be accomplished in a compact and pragmatic package. The design of compact 1 µm high power ps pump sources is well known to those skilled in the art. Through simple alteration of this design, additional and multiple wavelengths can be generated.

In another embodiment of the invention the OPA is seeded by a broadband seed source (where by broadband we mean a bandwidth that is greater than a sub-ns transform limited pulse) with central wavelength tuned to generate broadband idler pulses between 2 and 15 µm. This is important for applications that require broadband shaped pulses in order to increase the efficiency and selectivity of IHD ablation. [1]

In both of these embodiments, the most complex of the required components is the high power ps pump source. Various means are available to generate 1 µm, picosecond pulses with large (10 µJ to 1 mJ or greater) energy levels. A compact method is to generate ps pulses around 1 µm with a compact low power microchip laser [12], and amplify this pulse with a high power laser amplifier. Any 1 µm amplifier design can be used, for example, solid state diode pumped amplifiers or Yb doped large core or photonic crystal fiber amplifiers. The appropriate pump power is dictated by the desired output power and the nature of the required application of the laser. For example, the smallest, and most robust system would be based on fiber waveguide technology, including a Yb-doped fiber amplifier for the pump, a fiber coupled diode for the seed, and fiber optic components for combining the beams. However, higher output energies could be achieved for such a system with subsequent pump amplification using high power solid state amplifiers.

We also present a method of exploiting the interchangeable nature of the pump and signal beams in the process of OPA. This makes it possible to attain conversion efficiencies from the 1 µm pump laser to the mid-IR that are greater than the fundamental limit of a single stage OPA process, with as few as 3 additional optical components. The simple and robust nature of this new concept opens up the use of high power and high peak power mid-IR laser pulses to a wide variety of important applications.

A general schematic diagram of one embodiment of the system is shown in FIG. 1. This system produces a mid-IR sub-ns pulse with the desired wavelength $\lambda_3$ (and corresponding frequency $\omega_3$) by three wave mixing between a high energy sub-ns pulse with wavelength Xi (and corresponding frequency $\omega_1$) between 1.0 and 1.1 µm and a quasi-CW IR laser seed with good stability and spatial quality and with wavelength $\lambda_2$ (and corresponding frequency $\omega_2$) satisfying the relation $$1/\lambda_2 = 1/\lambda_1 - 1/\lambda_3.$$

If the desired idler wavelength $\lambda_3$ is in the range 2-15 µm and the pump wavelength $\lambda_1$ is between 1.0 and 1.1 µm, then the signal wavelength $\lambda_2$ must be in the range 1 to 2 µm.

Referring to FIG. 1, the picosecond high-power pump source is preferably a diode pumped laser system 1 with wavelength $\lambda_1$ between 1.0 and 1.1 µm that produces high energy (>10 µJ) narrowband picosecond pulses (1 to 1000 ps) with repetition rates <1 MHz. It is based on rare-earth doped optical materials pumped by near-infrared high power laser diodes. There are a variety of hosts doped by either Nd or Yb ions and each of these is optimal for certain modes of operation that are defined by average power, repetition rate, pulse energy, etc. The most well known examples are: Nd:YAG, Nd:YLF, Nd:YVO$_4$, Nd:GdVO$_4$, Yb:YAG, Yb:YVO$_4$, etc. The systems that are suitable for the present application are well known to those skilled in the art. These systems can include a sub-ns mode-locked oscillator and one or more high power amplifiers. The oscillator can be a solid-state laser or fiber laser resonator and can be actively or passively mode-locked (e.g. by a saturable absorber mirror (SESAM)). The oscillator pulses are picked out at a lower repetition rate and injected into the amplifier, which can be any combination of amplifiers known to those skilled in art (fiber amplifier, single-pass or multi-pass amplifier etc.). Alternatively, cavity dumped model-locked lasers or Q-switched-mode-locked-cavity dumped lasers could be used. However, the most compact and inexpensive embodiment is a passively or actively Q-switched microchip laser that seeds a high power amplifier. Microchip lasers routinely produce sub-ns pulses with energies on the order of 1 µJ and can readily be amplified to high energies by subsequent high power amplifiers comprised of matching laser gain materials.

The quasi-CW seed source 2 is a low power optical source with wavelength $\lambda_2$ tuned to $1/\lambda_2 = 1/\lambda_1 - 1/\lambda_3$. In principle, the mid-IR pulses can be generated without a seed source using OPG, but the resulting signal and idler beam would have bad spatial quality, large bandwidth and a short coherence length. By seeding the OPA with a narrowband quasi-CW seed beam, the spatial and spectral quality of the output pulses can be greatly improved. The seed beam should have approximately TEM00 beam quality, and be spatially matched to the pump in order to efficiently convert pump energy to the mid-IR idler beam at wavelength $\lambda_3$. The seed wavelength $\lambda_2$, should be in the 1 to 2 µm range, and fortunately this region overlaps with the telecom range where there is an abundance of high quality and inexpensive optical sources. The best candidates are CW diode pumped fiber lasers (that can be tuned by intra-cavity fiber Bragg gratings) and fiber coupled laser diodes that are now extremely precise and reliable. Commercial devices cover the whole S, C, and L band (from 1460 to 1625 nm), which maps into idler wavelengths in the 2.7 to 4 µm region. Custom made diodes could cover the 1.0 to 2.0 µm region, which maps into the 2 to 15 µm mid-IR region. Laser sources are available which are coupled to single mode fibers having average powers between 1 and 100 mW and excellent TEM00 spatial profiles.

The optical elements 3 and 4 are used for collimating and/or matching the spatial modes of the pump and seed beams to achieve good spatial overlap. Optical element 5 is used to combine the pump and seed beams for spatial overlap inside the first nonlinear crystal 6. These optical elements can include fiber optic components such as WDM splitters, combiners, fiber pigtailed collimators, etc. The mode matching and combining optics can be arranged in various ways not depicted in this schematic. For example, if pump source 1 includes a pump amplifier, used to amplify the $\lambda_1$ pulses of another laser, which is capable of transmitting wavelengths $\lambda_2$ without deleterious effects, the combining optics could be placed between this pump amplifier and the original source of the $\lambda_1$ pulses. By placing the combining optics before a fiber amplifier, the waveguide will cause the modes of the two beams to be similar at the amplifier output, and will ensure collinear propagation into the nonlinear crystals.

After the OPA stage 7, the laser pulses, including the desired mid-IR idler, are separated or filtered and then steered with beam delivery elements 8 towards the desired location or target 9.

This laser system includes a bulk nonlinear crystal 6 where the optical field with wavelength $\lambda_3$ is generated as an idler field in the OPA process between wavelengths $\lambda_1$ and $\lambda_2$. The OPA stages can be composed of any non-linear media that is suitable for these combinations of wavelengths (e.g. KTA, Potassium Titanyl Phosphate (KTP), Rubidium Titanyl Phosphate (RTP), Rubidium Titanyl Arsenate (RTA), Lithium Niobate (LiNbO$_3$ or LNB), Lithium Tantalate (LiTaO$_3$ or LTA), MgO:LiNbO$_3$, Silver Thiogallate (AgGaS$_2$), Silver Selenogallate (AgGaSe$_2$), Gallium Selenide (GaSe), Mercury Thiogallate HgGa$_2$S$_4$ (HGS), Lithium Thioindate (LiInS$_2$) Lithium Selenoindate (LiInSe$_2$), Zinc-Germanium Diphosphide (ZnGeP$_2$), etc.) If a single crystal is to be used it must be capable of producing sufficient gain to achieve significant pump depletion. In an additional embodiment, this design could include a waveguide containing nonlinear optical material for pre-amplification between elements 5 and 6 to supplement the gain of the first OPA stage.

The phase matching conditions of non-linear optical crystals can be determined by solving the following equations:

$$\omega_3 = \omega_1 - \omega_2$$

$$k_1 = k_2 + k_3$$

Where $\omega_i$ is the frequency of the incident photons and $k_i = n_i/\lambda_i$ is the momentum, where $\lambda_i$ is the wavelength of the incident photons and $n_i$ is the index of refraction of the nonlinear crystal at that wavelength. For materials such as these, the index of refraction is a function of wavelength and propagation direction relative to the optical axes of the crystal. It is also a function of polarization, thus there are two different indices of refraction for a single direction of propagation. For uniaxial crystals, these are the "ordinary" and the "extraordinary" indices of refraction. For biaxial crystals, they are referred to as the "fast" and the "slow," where the fast index is the smaller of the two indices. Thus there are different permutations of polarizations for the different wavelengths that can lead to phase matching, which are defined here as follows:

$$k_1^{fast} = k_2^{slow} + k_3^{slow} \text{(type I)}$$

$$k_1^{fast} = k_2^{fast} + k_3^{slow} \text{(type IIa)}$$

$$k_1^{fast} = k_2^{slow} + k_3^{fast} \text{(type IIb)}$$

$$k_1^{slow} = k_2^{slow} + k_3^{fast} \text{(type IIIa)}$$

$$k_1^{slow} = k_2^{fast} + k_3 slow \text{(type IIIb)}$$

Although the theory of three wave mixing has been fully understood for many years, and exploited in numerous applications, the generation of high power light by parametric amplification has predominantly used uniaxial crystals with type I phase matching. We have designed and demonstrated various new phase matching schemes in our work. In the case of KTA, such processes have not previously been demonstrated, particularly collinear and noncollinear type IIb phase matching in the XZ crystal plane. The exact phase matching angle is determined by the wavelengths, temperature of the crystal and the noncollinear angle between the beams.

In one embodiment of this invention we present a number of novel amplification methods based on nonlinear three wave mixing in the biaxial crystal KTA, which also apply to other members of this crystal family including (KTP, RTP, RTA, etc.) Phase matching conditions with high nonlinear coefficients can be achieved in KTA with a number of configurations as described below. These crystals, when pumped in the near-IR around 1 µm are capable of amplifying and generating wavelengths in the range of 1 to 4 µm. KTA is a superior medium for these wavelengths because of its low absorption in the mid-IR, high damage threshold and robust material properties. Other configurations and crystals exist which can amplify these pulses, however KTA enables an elegant and compact design that is able to achieve high gain from single bulk crystals. KTA crystals can be manufactured with large dimensions (>1 cm) and thus are perfectly suited for high power mid-IR generation. The optical damage threshold of these crystals for 1 µm, 100 ps pulses is greater than 1 GW/cm$^2$, and increases with shorter pulses.

Efficient amplification in KTA of the optical spectrum around 1.6 µm with a pump around 1 µm, resulting in the generation of a 3 µm idler, can be accomplished in a number of ways. The following examples are listed as novel configurations capable of sufficient gain to allow efficient conversion of energy from the pump wavelength to that of the seed and idler. The phase matching angle for both type IIa and IIb in the XZ crystal plane of a bulk KTA crystal is shown as a function of wavelength in FIG. 2a.

Figure 2:
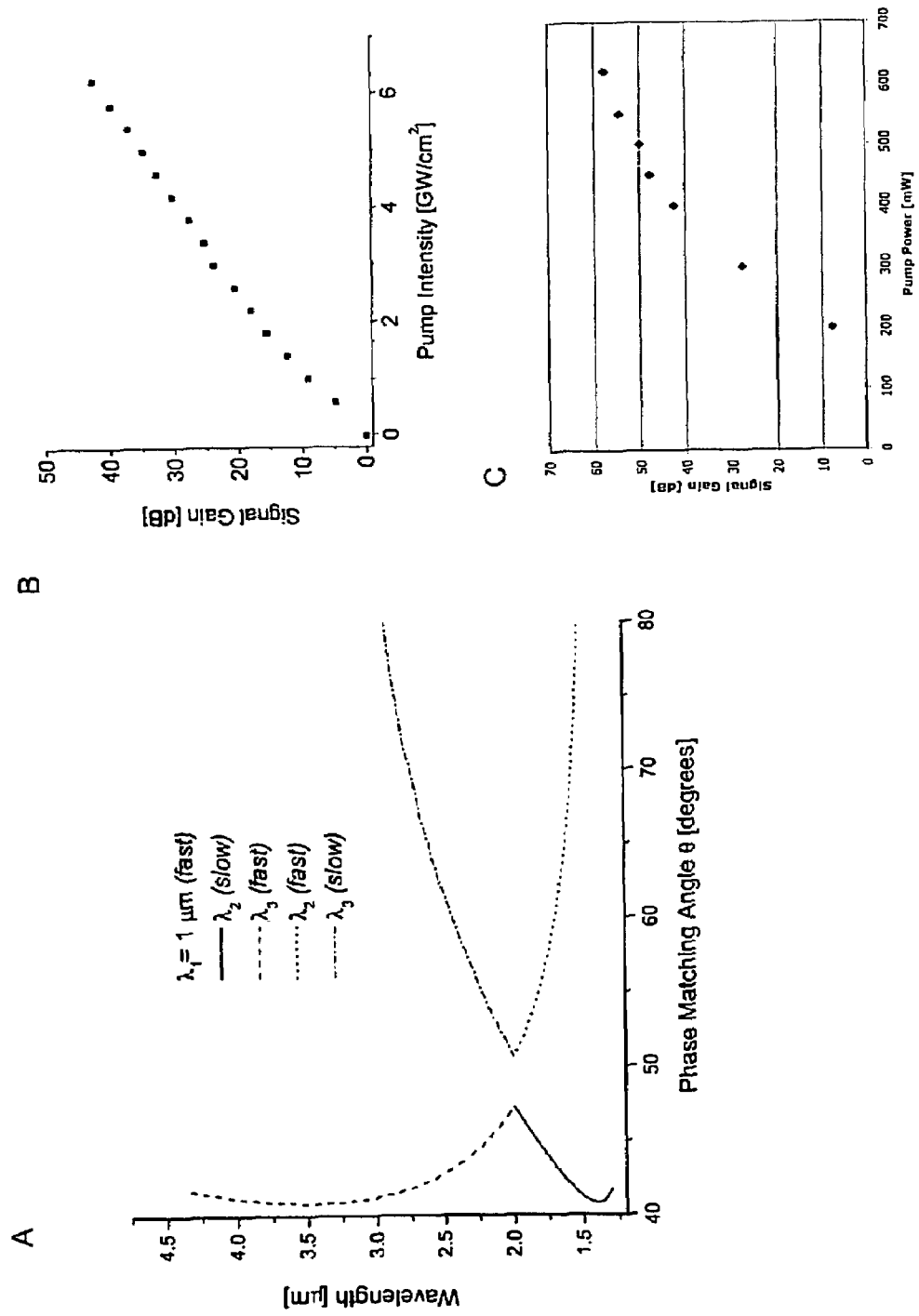
FIG. 2 shows A: Type II phase matching conditions in the XZ plane of KTA crystals. B: Signal ($\lambda_2=1.56$ µm) gain as a function of pump ($\lambda_1=1.053$ µm) intensity for type IIb phase matching in a 15 mm long KTA crystal with 0.47 mm radius beams. C: Signal ($\lambda_2=1.6$ µm) gain as a function of pump ($\lambda_1$=1.053 µm) power for type IIa phase matching in a double passed 20 mm long KTA crystal.
Figure 3:
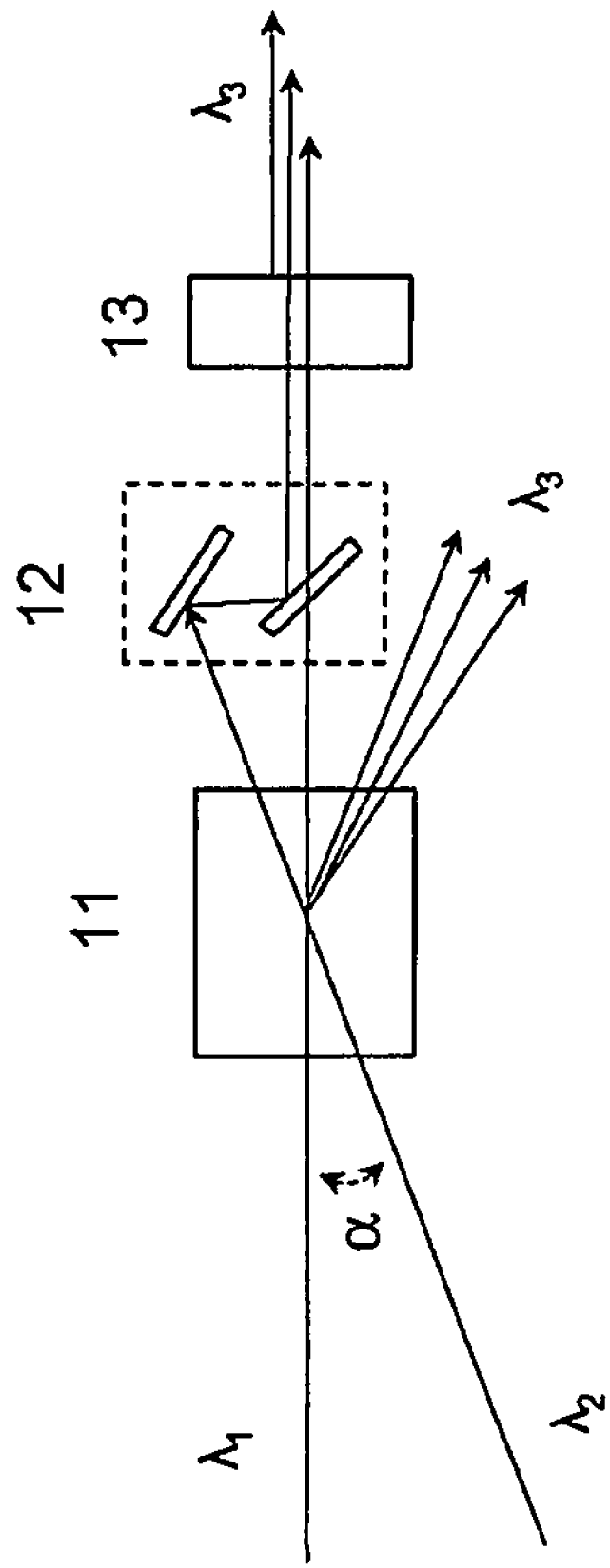
FIG. 3 shows the utilization of non-collinear phase matching geometries to increase the amplification bandwidth of an OPA stage, while still generating good spatial quality high energy mid-IR output beams.

Collinear type IIb phase matching occurs for these wavelengths around $\theta\sim45°$ and $\phi\sim0°$ or $\theta\sim35°$ and $\phi\sim90°$. Where $\theta$ is the polar angle measured from the crystal's z-axis and $\phi$ is the azimuthal angle measured from the x-axis toward the y-axis of the crystal. We have demonstrated single pass small signal gains greater than 40 dB, as shown in FIG. 2b. The bandwidth of this process is approximately 15 nm/cm. The amplification bandwidth can be increased by introducing a noncollinear angle between the incident pump and seed pulses. This bandwidth increase is due to better matching of the group velocities of the different pulses. The amplification bandwidth in KTA can be greater than 100 nm, with a noncollinear angle of approximately 3.5°. However, noncollinear phase matching results in angular dispersion of the idler pulse that is proportional to the noncollinear angle. This effect can limit the usefulness of the resulting idler pulses. Nonetheless, as illustrated in FIG. 3, a noncollinear OPA stage 11 can still be used to amplify broad bandwidth seed pulses to high powers where the mid-IR idler pulses of acceptable spatial quality are generated by overlapping (element 12) the transmitted pump and broadband amplified signal beams in a subsequent collinear OPA stage 13 with a nonlinear crystal thin enough to support the desired bandwidth.

Collinear Type IIa phase matching occurs at $\theta\sim70°$ and $\phi\sim0°$ or $\theta\sim65°$ and $\phi\sim90°$, where there is no walk-off between the Poynting vectors of the signal and pump beams. Thus very long (>20 mm) bulk crystals can be used even with small beam diameters (<0.5 mm) to amplify these wavelengths with very high gain. This nonlinear process is ideal for the amplification of 1.6 µm and the generation of 3 µm pulses from low power 1.6 µm quasi-CW seeds. The bandwidth of this process is approximately 10 nm/cm, allowing the amplification of picosecond pulses in long bulk crystals with low angular divergence, making the alignment of these crystals less critical. Small signal gain greater than 40 dB can be achieved for 100 ps pulses in a single pass 15 mm long crystal, as shown in FIG. 2c.

Figure 4:
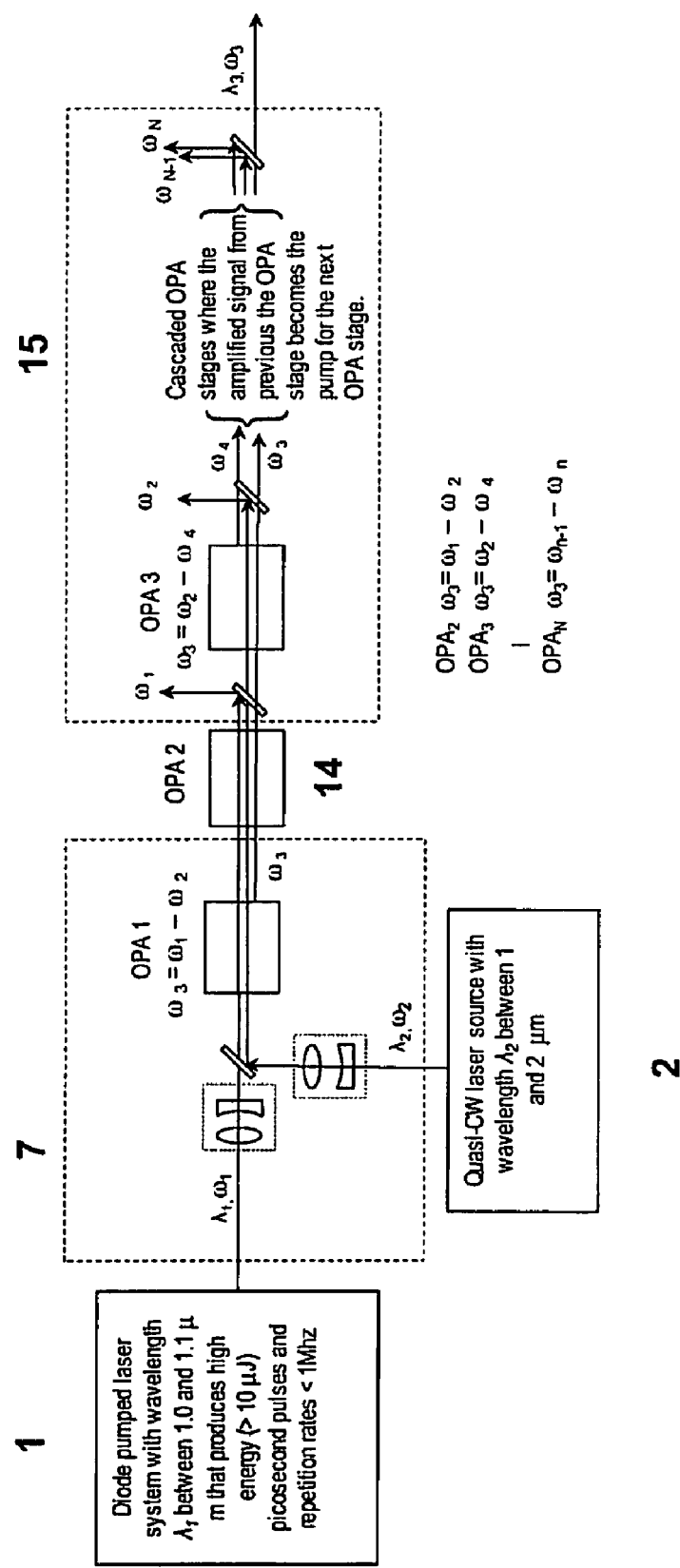
FIG. 4 shows the addition of subsequent OPA stages, including cascaded OPA stages.

In some cases the gain from a single pass of the OPA is not large enough to achieve significant conversion of the pump energy to the mid-IR idler pulses. In this case one or more additional passes through the nonlinear crystal or additional nonlinear crystals can be used to increase the energy conversion, as shown in FIG. 4. In the case of an undepleted pump, additional passes through the same OPA stage, or additional independent stages can utilize the undepleted pump from OPA stage 7 for the second pass or independent OPA stage 14. Additional optical elements (for example lenses or mirrors) can be included between the first OPA stage 7 and subsequent passes or nonlinear crystals 14 in order to optimize the laser beam diameter and intensity for further amplification or mixing.

The choice of crystals for subsequent stages is made depending on whether or not the signal or idler pulses from the first OPA stage will be used for seeding the second OPA stage. Using the signal from the first OPA stage should allow larger OPA gain (due to its smaller wavelength). On the other hand the idler beam divergence that comes from the first OPA stage is smaller due to its larger wavelength. If both pulses are used, the distance between the OPA stages would have to be adjusted to maintain the phase relationship between the pump, signal and idler beams, which influences the direction of energy flow in three-wave mixing processes. The tolerance for this distance is on the order of mm and can be easily achieved.

It should be noted that since the energy of the input pump pulse is large, the diameters of the input laser beams can be >0.5 mm with correspondingly large Raleigh ranges. If a collinear phase matching geometry is used, the non-linear crystals can be placed immediately one after the other without additional telescopes and steering mirrors, which can lead to a particularly simple and elegant design.

For every signal photon at $\lambda_2$ created in the OPA, an idler photon at $\lambda_3$ must be created as well. Thus, the total number of signal and idler photons created in the OPA must be the same, and hence the ratio of the total energies of the amplified signal and mid-IR idler optical fields should be the same as the ratio of signal and idler photon energies or the inverse ratio of their wavelengths. In the present case the mid-IR idler wavelength $\lambda_3$ is in the range 2-15 µm and the signal wavelength $\lambda_2$ is in the range 1 to 2 µm. Thus, although pump energy depletion can be large, a greater proportion of the pump energy will be transferred to the signal wavelength $\lambda_2$ with a smaller fraction of that energy converted to the desired mid-IR pulse at wavelength $\lambda_3$.

The total conversion efficiency can be further improved through the addition of several more OPA stages in a cascade, where the amplified signal ($\lambda_2$) from one OPA stage becomes the pump for the next one. Referring again to FIG. 4, the optical field $\lambda_3$ is mutual to all OPA stages and acquires more energy from each cascaded OPA stage 15. Additional optical elements (for example lenses or mirrors) can be included between subsequent optical parametric amplifier stages in order to optimize laser beam diameters and intensities for the three wave mixing processes.

For example, for generating picosecond pulses in the very important region around 3 µm, the initial signal wavelength $_2$ is around 1.6 µm. After the first OPA stage operating at 70% pump depletion as an example, the conversion efficiencies to 1.6 and 3 µm fields are around 45% and 25% respectively. By adding one more OPA stage immediately after the first stage, where the 1.6 µm pulses becomes a new pump and the 3 µm pulses a new seed, we can get approximately 30% energy conversion from the amplified 1.6 pulses to the 3 µm pulses. This results in an approximately 40% overall conversion from the 1 μm pump pulse to the 3 μm mid-IR pulse. The benefit in increasing the conversion efficiency gets much larger as one moves deep into the mid IR. For example it would be possible to get 15-25% of conversion efficiency from 1 μm pump to 6 μm picosecond pulses in just 3 OPA stages. This result with 6 μm pulses should be compared to the typical value of less than 5% with conventional conversion methods.

Figure 5:
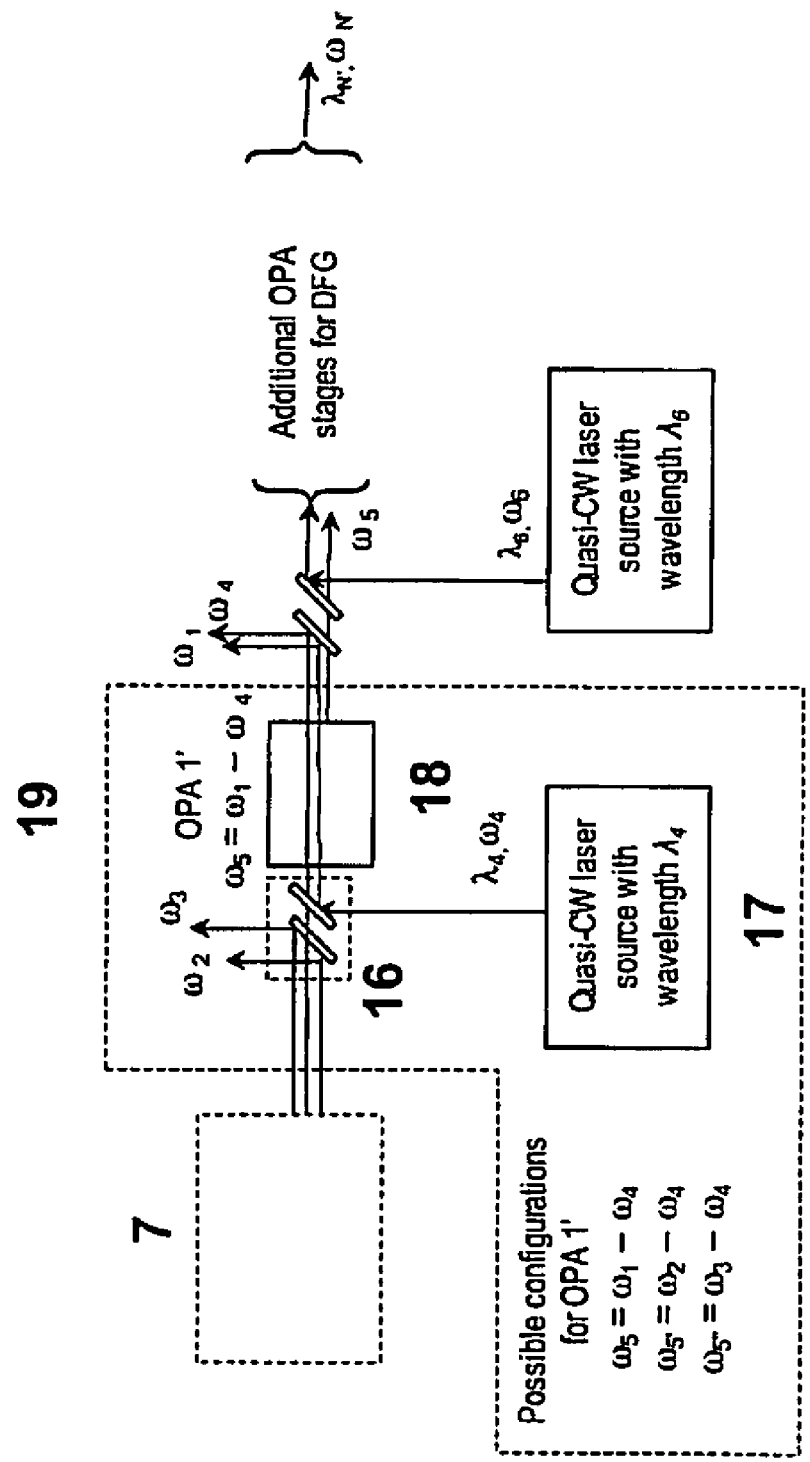
FIG. 5 shows the addition of subsequent OPA stages seeded by additional quasi-CW sources for the generation of more wavelengths.

In another embodiment of this invention, seeding can be performed with additional quasi-CW beams at different wavelengths, to generate additional mid-IR idler wavelengths. This is illustrated in FIG. 5, where an additional quasi-CW laser source 17 having new wavelength $\lambda_4$ is combined, using element 16, with one of the outputs of one of the OPA stages 7. The combined beams are then directed to nonlinear crystal 18, which generates subsequent pulses with wavelengths $\lambda_4$ and $\lambda_5$ through a three wave mixing process. In addition, additional quasi-CW sources can be used in further DFG stages 19 to generate more wavelengths.

In another embodiment of this invention, an OPA stage is seeded with a broadband source with central wavelength tuned to generate broadband mid-IR pulses between 2 and 15 μm. In addition, the broadband pulses are shaped temporally and spectrally in order to increase the efficiency and selectivity of IHD ablation. This is important for ablation of soft tissue in medical applications of IHD, as the increased efficiency and selectivity can reduce deleterious collateral damage in the surrounding tissue. The shaping of the broadband mid-IR pulses can be done directly at mid-IR wavelengths using current technology that is well know to those skilled in the art. Alternatively, the broadband seed pulses at wavelengths between 1 and 2 μm can be shaped using well developed techniques that are well know to those skilled in the art, including robust telecom components. The broadband seed pulses with wavelengths between 1 and 2 μm can be produced by any method well known to those skilled in the arts, including broadband diode sources and mode-locked lasers. Also, in order to gain additional bandwidth and wavelengths, additional non-linear processes may be added between the OPA stages. For instance, an appropriately shaped mid-IR pulse may be used to generate broadband white light through non-linear super-continuum generation, which in additional OPA stages can then be further amplified to higher powers or transferred to larger wavelengths while keeping the super-continuum bandwidth.

Sometimes it is desirable to have several mid-IR wavelengths at the same target spot simultaneously. Since the disclosed systems generate several laser beams with different IR frequencies $\lambda_1, \lambda_2, \ldots, \lambda_n$, any set of these beams can be combined and used as a single laser beam afterwards. The techniques for doing this are well known to those skilled in art.

Figure 6:
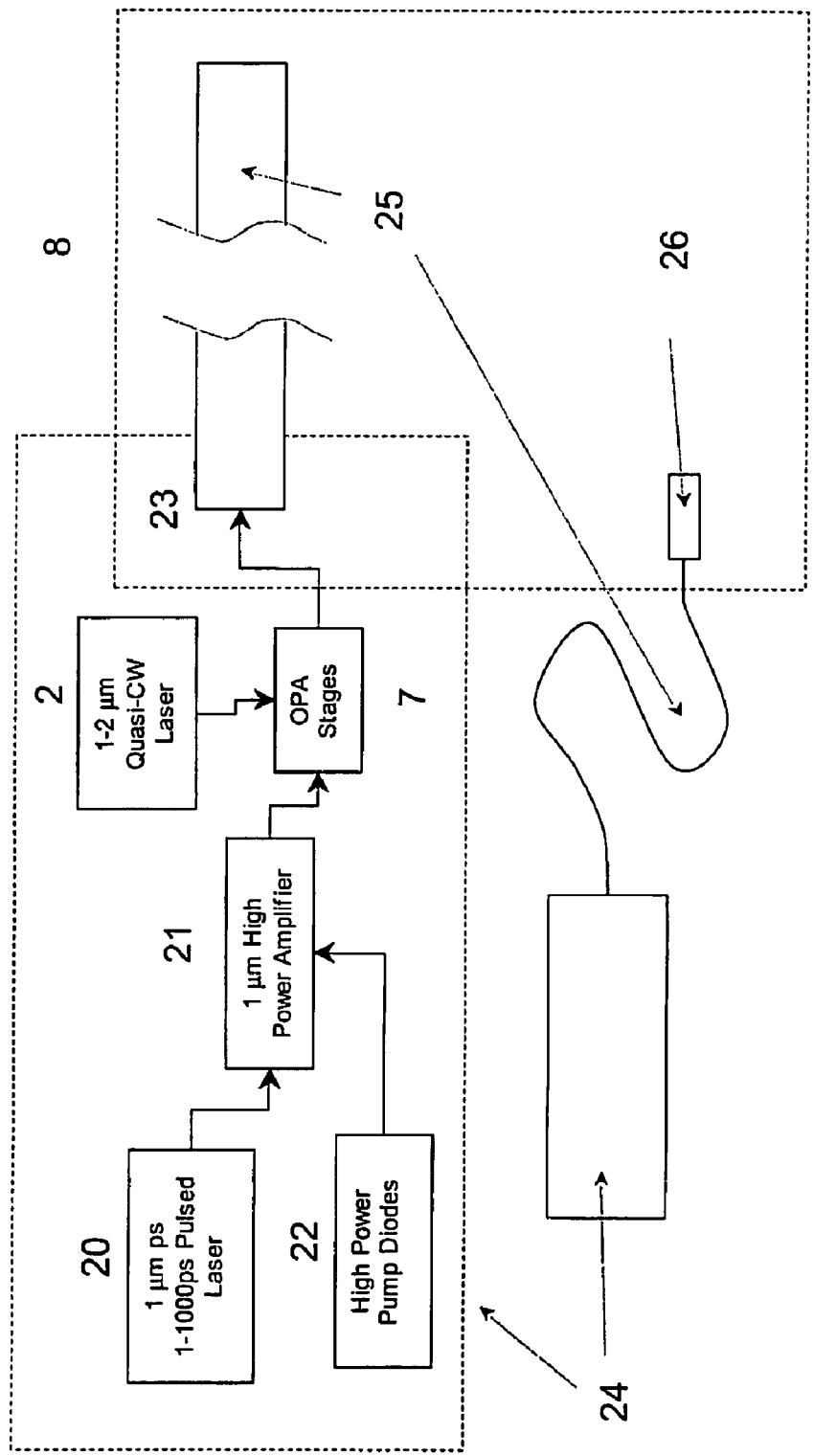
FIG. 6 shows an embodiment of the invention where the device is split into a laser head, a fiber beam delivery mechanism and a removable/replaceable fiber tip.
Figure 7:
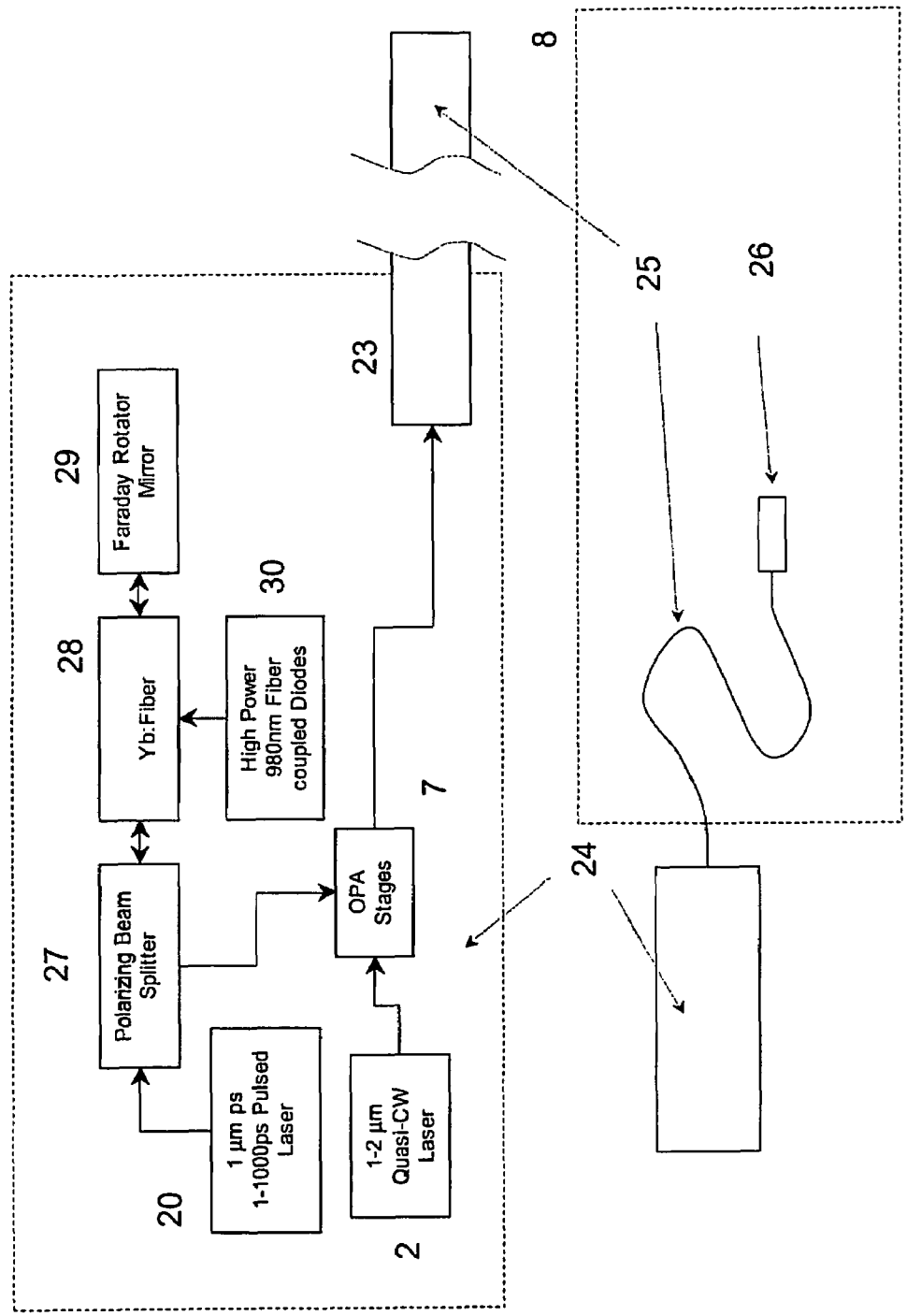
FIG. 7 shows an embodiment of the invention where the high energy pump pulses are produced using a Yb fiber laser amplifier with a Faraday rotator mirror for polarization control.
Figure 8:
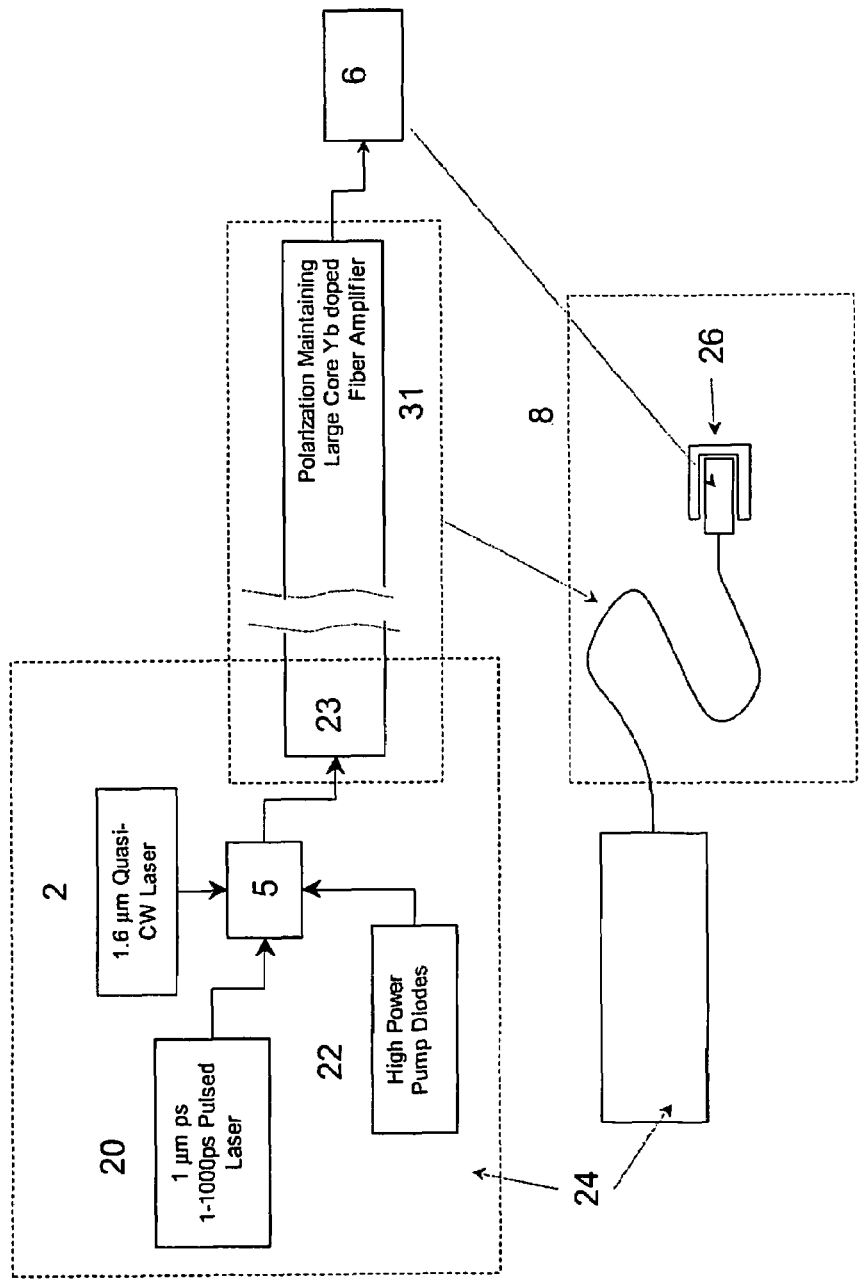
FIG. 8 shows an embodiment of the invention where a large core polarization maintaining Yb fiber laser amplifier is used to produce the high energy pump pulses.
Figure 9:
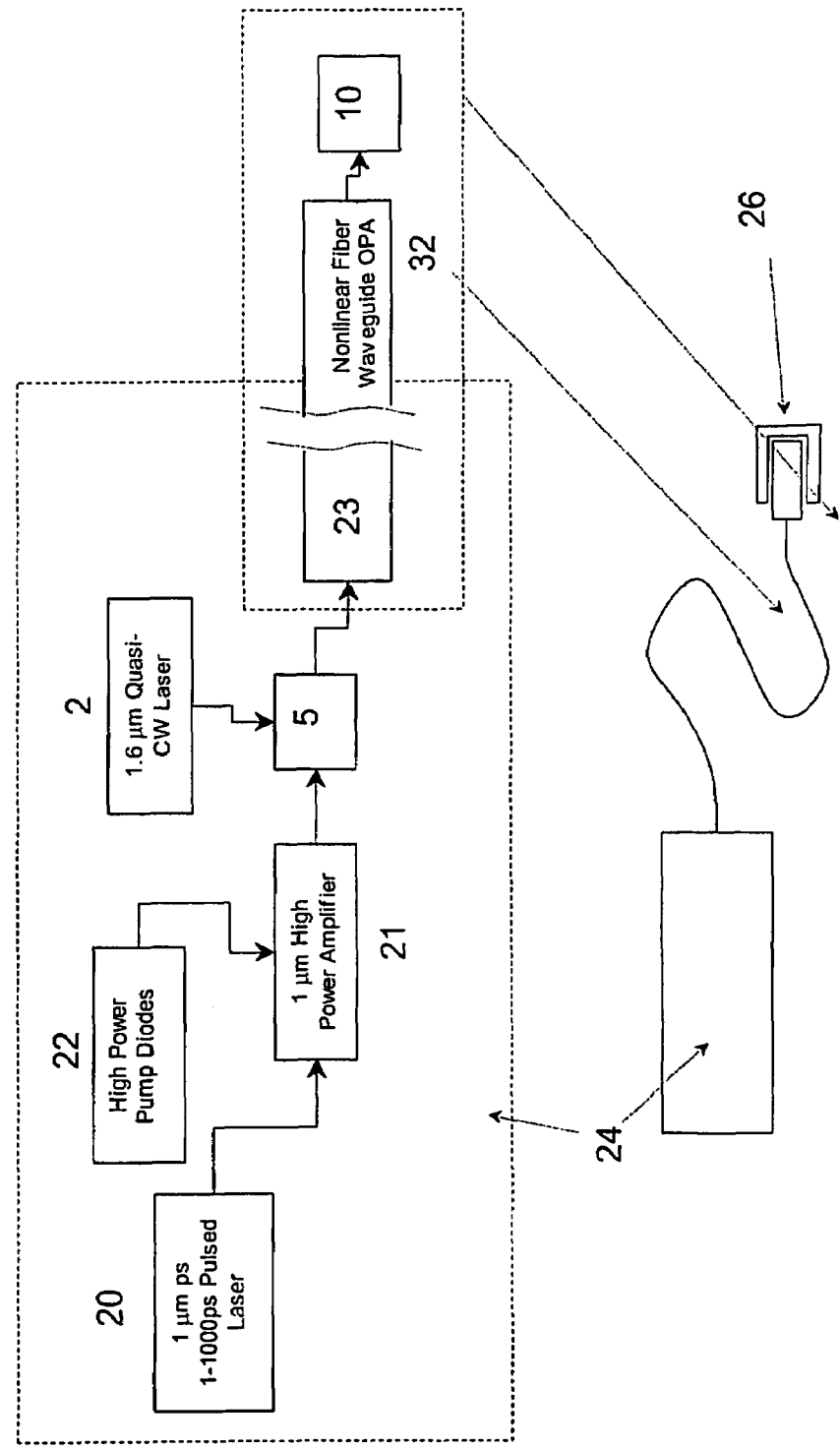
FIG. 9 shows an embodiment of the invention where the OPA consists of a non-linear crystal fiber waveguide.

As shown in FIG. 6, for practical applications in medical or dental surgery the laser system could be comprised of three packages: a laser head 24, flexible fibre 25 and a hygienic tip 26. The three subsystems can be comprised of different components arranged in a number of ways as illustrated in FIGS. 6 to 9.

Figure 10:
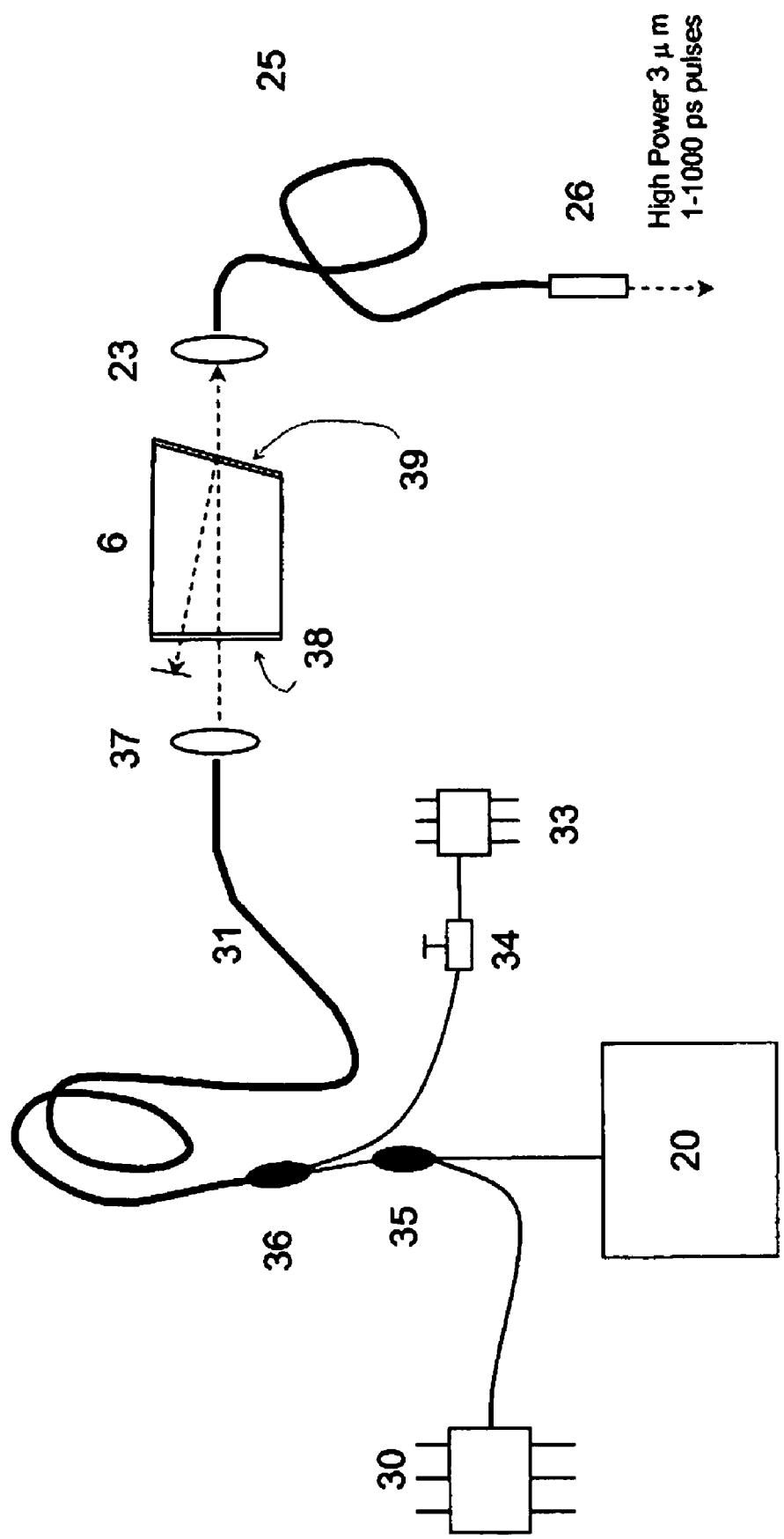
FIG. 10 shows an embodiment of the invention, where the laser system uses fiber waveguide technology that is designed to include few free space components.

Laser Head which is comprised of the following elements:
 1.0 to 1.1 μm, picosecond pulsed laser 20, e.g. a pulsed laser diode, microchip laser, Yb doped fiber oscillator, etc.
 diode lasers 22 for pumping the solid-state amplifiers.
 1 to 2 μm seed 2, from either a quasi-CW laser diode, with broad or narrow bandwidth or a mode-locked oscillator whose output is shaped into a broadband picosecond pulse.
 Beam shaping and combining optics And in some cases the following:
 Yb doped fiber 28, including large core and photonic crystal fibers [13], along with 980 nm pump diodes 30 (see FIG. 7).
 Faraday mirror 29 and polarizing beam splitter 27 to correct for polarization changes in the Yb doped fiber (see FIG. 7) [14]
 Polarization maintaining Yb doped fiber 31 (see FIG. 8)
 An amplitude modulator, e.g. fast fiber coupled electro- or acousto-optic modulators for either ~1 or 1.6 μm.
 Compact rare earth doped solid-state amplifier 21 e.g: Nd:YAG, Nd:YLF, Nd:YVO4, Nd:GdVO4, Yb:YAG, Yb:YVO4 etc.
 OPA stage 7 comprising one or more bulk nonlinear crystals.
 Additional cascaded OPA stages 10.
 Fiber coupling optics 23.
 Spectral and temporal pulse shaping optics.
Flexible transport fiber 25, which includes some of the following:
 Waveguide capable of transmitting high power mid-IR pulses, including hollow core fiber waveguides [15]
 Polarization maintaining Yb doped fiber 31 followed by an OPA stage 6 (see FIG. 8)
 nonlinear optic waveguide or fiber 32 (see FIG. 9)
 Focusing optics
Hygienic Tip 26, which includes some of the following:
 Protective fiber tip
 Replaceable applicator
 Collimating or focusing optics
 Scanning optics which quickly change the beam direction For example, a very compact system could be built as in FIG. 10, where the laser head contains a lower power ~1 μm, picosecond pulsed laser 20 which is then combined with the output of a lower power 1.6 μm fiber coupled quasi-CW laser diode 33 and a high power ~980 nm pump laser diode 30 using fiber WDM's 35 and 36. The polarization of the 1.6 μm seed is controlled by a fiber optic component 34. The combined light is coupled into a Yb doped large core or photonic crystal fiber 31 which is pumped by the 980 nm light, which amplifies the ~1 μm light to energies greater than 100 μJ levels and transmits the 1.6 μm seed. The output of the fiber amplifier is directed by optic 37 onto a long bulk KTA crystal 6 cut for type II phase matching with high power antireflection coatings 38 on the input face, resulting in high power amplified 1.6 μm and generated 3 μm pulses. The 1 μm and 1.6 μm pulses are separated with a dichroic coating 39 which transmits only the 3 μm pulses. These pulses are coupled to a flexible waveguide 25 designed for high power 3 μm pulses, which has on the output end an assembly for mounting a replaceable tip, that simultaneously prevents damage to the end of the transport fiber and enables the tip to be hygienic.

Figure 11:
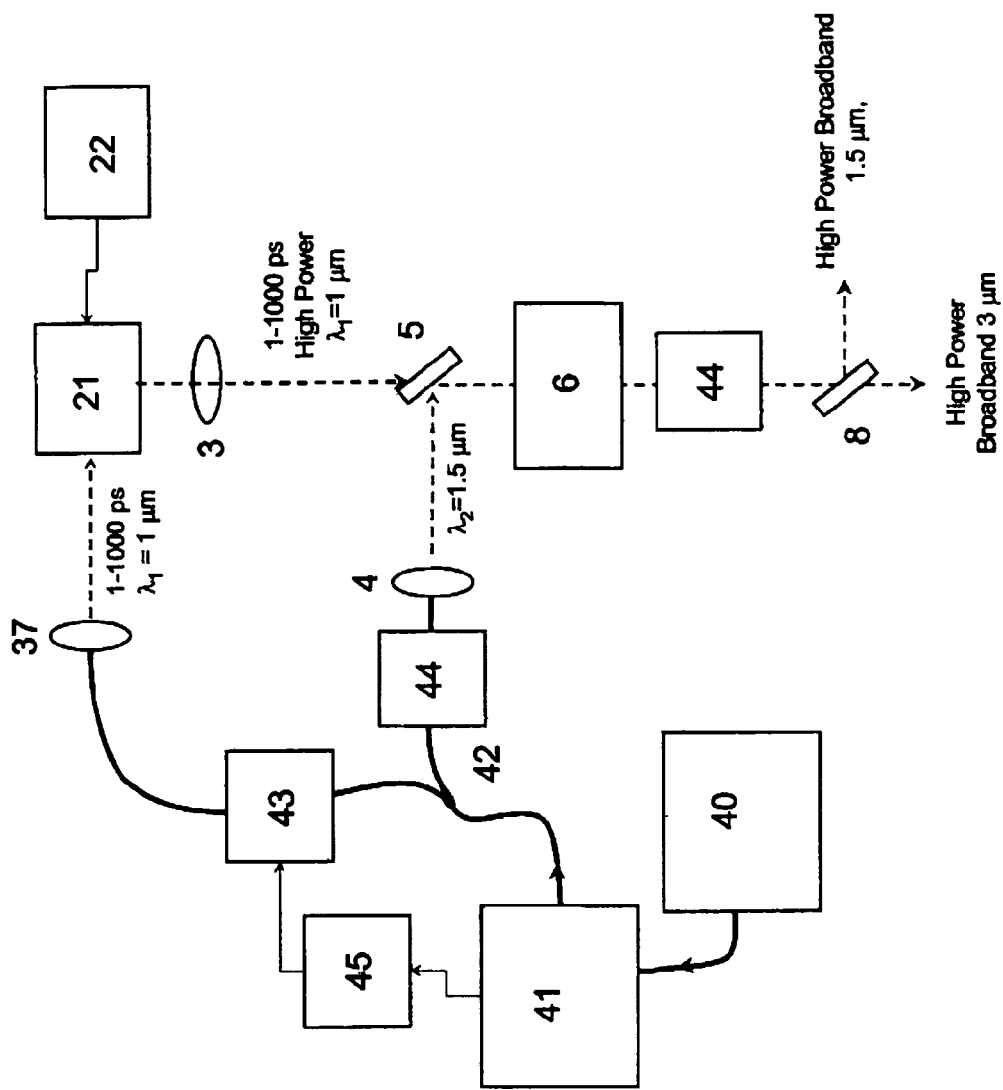
FIG. 11 shows an embodiment of the invention in a laser apparatus using fiber waveguide technology to generate broadband shaped mid-IR pulses with a limited number of free space components.

As another example, a similar system, but with broadband output pulses with wavelengths around 3 μm, could be built as shown in FIG. 11. In this system the timing of the pulses of a mode locked Yb doped fiber oscillator 41 with wavelengths around 1 μm and a Er doped fiber oscillator 40 with wavelengths around 1.55 μm are passively synchronized using cross-phase modulation within the Yb oscillator cavity [16, 17]. The two wavelengths are split by WDM 42. In order to control the final mid-IR pulse energy, the amplitude of the 1 μm pulse is modulated by an electro- or acouto-optic component 43 which is synchronized to the laser by clock signal 45. The 1 μm pulse is then amplified by solid state amplifier 21, and the two wavelengths are then recombined in OPA 6 in order to generate mid-IR pulses around 3 μm. With the addition of a pulse shaper 44, broadband temporally and spectrally shaped mid-IR pulses will be produced in a compact and robust laser system.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

[1] R. J. D. Miller, "Laser selective cutting by impulsive heat deposition in the IR wavelength range for direct-drive ablation" U.S. patent application Publication XXX. (2005).
[2] G. R. Holtom, R. A. Crowell, X. S. Xie: "High-repetition-rate femtosecond optical parametric oscillator-amplifier system near 3 um", J. Opt. Soc. Am. B 12, (1995) p 1723
[3] P. Hamm, R. Kaindl, J. Stenger. "Noise suppression in femtosecond mid-infrared□light sources", Opt. Lett. 25, (2000) p 1798
[4] R. A. Kaindl, M. Wurm, K. Reimann, P. Hamm, A. M. Weiner, M. Woerner, "Generation, shaping, and characterization of intense femtosecond pulses tunable from 3 to 20 um" J. Opt. Soc. Am. B 17, (2000) p 2086
[5] Rotermund, F. Petrov, V., "Femtosecond noncollinear parametric amplification in the mid-infrared" Opt. Comm., 169 (1999) p 183
[6] L. Carrion, J. P. Girardeau-Montaut "Performance of a new picosecond KTP optical parametric generator and amplifier" Opt. Comm., 152 (1998) p 347
[7] K. Finsterbusch, R. Urschel, H. Zacharias, "Tunable, high-power, narrow-band picosecond IR radiation by optical parametric amplification in KTP", Appl. Phys. B 74, (2002) p 319
[8] K. Finsterbusch, A. Bayer, H. Zacharias, "Tunable, narrow-band picosecond radiation in the mid-infrared by difference frequency mixing in GaSe and CdSe" Appl. Phys. B 79, (2004) p 457
[9] E Rotermund, V Petrov, F. Noack, V. Pasiskevicius, I. Hellstrom, F. Laurel, H. Hundertmark, P. Adel and C. Fallnich, "Compact all-diode-pumped femtosecond laser source based on chirped pulse optical parametric amplification in periodically poled KTiOP0$_4$", Electronic Lett., 38, (2002) p 561
[10] K. Fradkin-Kashi, A. Arie, P. Urenski, and G. Rosenman, "Mid-infrared difference frequency generation in periodically poled KTiOAsO$_4$ and application to gas sensing", Opt. Lett., 25, (2000) p 743
[11] Y. Matsuura, M. Miyagi, "Er:YAG, CO, and CO$_2$ laser delivery by ZnS-coated Ag hollow waveguides," *Appl. Opt.* 32, (1993), p 6598.
[12] Braun, B.; Kartner, F. X.; Zhang, G.; Moser, M.; Keller, "56-ps passively Q-switched diode-pumped microchip laser" Opt. Lett., 22, (1997), p 381
[13] F. Di Teodoro and C. Brooks, "1.1 MW peak-power, 7 W average-power, high-spectral-brightness, diffraction-limited pulses from a photonic crystal fiber amplifier," Opt. Left. 30, (2005) p 2694
[14] Yamashita, S., Hotate, K, and Ito, M.: 'Polarization properties of a reflective fiber amplifier employing a circulator and a Faraday rotator mirror', J. Lightwave Technol., 14, 3 (1996) p 385
[15] Y. Matsuura, A. Hongo, M. Miyagi, "Dielectric-coated metallic hollow waveguide for 3-um Er:YAG, 5-um CO, and 10.6-um CO$_2$ laser light transmission", App. Opt., 29, (1999) p 2213
[16] R. J. D. Miller, K. Franjic, D. Kraemer, M. Piche, "Method and apparatus for high power optical amplification in the infrared wavelength range (0.7-20 mum)", U.S. patent application Publication 20050271094. (2005).
[17] M. Rusu, R. Herda, O. G. Okhotniko, "Passively synchronized two-color mode-locked fiber system based on master-slave lasers geometry", Opt. Express 12, (2004) p 4719

Therefore what is claimed is:

1. A method of producing high power picosecond (ps) mid-infrared (IR) laser pulses having a wavelength $\lambda_3$ between 2 and 15 µm, comprising the steps of:
   a) producing high energy pump pulses with a wavelength $\lambda_1$, between about 1 and about 1.1 µm, a pulse duration between about 1 and about 1000 ps, and an energy larger than about 10 µJ;
   b) producing a low power continuous wave (CW) laser beam, having a power in a range between about 1 to about 100 mW, with a wavelength $\lambda_2$, satisfying a relation $1/\lambda_2=1/\lambda_1-1/\lambda_3$ wherein said wavelength $\lambda_2$ is between about 1.19 to 2 µm;
   c) directing, focusing and combining said pump pulses and said CW laser beam in such a way that they have substantial spatial overlap, and directing the combined pump pulses and CW laser beam into at least one optical parametric amplifier each having at least one bulk non-linear optical crystal, without said CW laser beam passing through an optical parametric oscillator before entering said optical parametric amplifier, with the peak intensity of the pump pulses sufficient such that high energy picosecond mid-IR pulses at wavelength $\lambda_3$ between 2 and 15 µm are produced through three wave mixing between said spatially overlapped pump pulses and CW laser beam in said at least one bulk non-linear optical crystal; and
   d) directing said high energy picosecond mid-IR pulses at wavelength $\lambda_3$ between 2 and 15 µm from an output of said at least one optical parametric amplifier to a desired location.

2. The method according to claim 1 wherein said CW laser beams are generated directly by laser diodes or fiber coupled laser diodes.

3. The method according to claim 1 wherein said high energy pump pulses are produced by any one of a microchip laser, gain switched laser diode and Yb fiber laser, whose output is amplified in at least one Yb doped fibre, producing high energy (>10 µJ) narrowband 1 to 1000 ps pulses with repetition rates <1 MHz.

4. The method according to claim 1 wherein said high energy pump pulses are produced by any one of a microchip laser, gain switched laser diode and Yb fiber laser, whose output is amplified in at least one multi-pass diode pumped solid-state laser amplifier, producing high energy (>10 µJ) narrowband 1 to 1000 ps pulses with repetition rates <1 MHz.

5. The method according to claim 1 wherein said high energy pump pulses are produced by any one of a microchip laser, gain switched laser diode or Yb fiber laser, whose output is amplified by any combination of Yb doped fibre amplifiers and multi-pass diode pumped solid-state laser amplifiers, producing high energy (>10 µJ) narrowband 1 to 1000 ps pulses with repetition rates <1 MHz.

6. The method according to claim 1 wherein said at least one optical parametric amplifier is a first optical parametric amplifier in a cascade of optical parametric amplifiers, wherein an amplified field from one optical parametric amplifier becomes a pump field for at least one of the subsequent optical parametric amplifiers in said cascade, producing additional wavelengths $\lambda_4$ through $\lambda_n$, where n is determined by the number of cascaded optical parametric amplifiers.

7. The method according to any of claim 6 wherein said optical parametric amplifiers in said cascade are seeded with additional CW laser beams at different wavelengths.

8. The method according to claim 1 wherein said pump pulses have a $\lambda_1$ and said continuous wave (CW) laser beam has a $\lambda_2$ such that said high energy picosecond mid-IR pulses have wavelength $\lambda_3$ between 2.8 and 3.1 µm corresponding to the OH-stretch absorption band of liquid water.

9. The method according to claim 6 wherein said high energy picosecond mid-IR pulses with wavelength $\lambda_3$ are further amplified in at least a second optical parametric amplifier in said cascade that uses as a pump pulse the amplified output of said first optical parametric amplifier at said wavelength $\lambda_2$.

10. The method according to claim 1 wherein said pump pulses have a $\lambda_1$ and said continuous wave (CW) laser beam has a $\lambda_2$ such that said high energy picosecond mid-IR pulses have a wavelength $\lambda_3$ between approximately 5.5 and 6.5 µm corresponding to amide absorption bands.

11. The method according to claim 1 including additional optical combining, separating and/or filtering elements after which said laser beam with wavelength $\lambda_i$ is overlapped with one or several of said laser beams with wavelengths $\lambda_1, \lambda_2, \ldots, \lambda_n$ and used as a single laser beam thereafter.

12. The method according to claim 1 wherein a power of said CW laser beam is modulated in time such that there is temporal overlap with at least some of said high energy pump pulses.

13. The method according to claim 1 wherein the energy of said high energy picosecond mid-IR pulses at wavelength $\lambda_3$ is adjusted by controlling a power of said CW laser beam.

14. The method according to claim 1 wherein the energy of said high energy picosecond mid-IR pulses at wavelength $\lambda_3$ is adjusted by controlling the energy of said high energy pump pulses.

15. The method according to claim 12 wherein the power of said high energy pump pulses and/or said continuous wave (CW) laser beam is controlled using any one of electro-optic, acousto optic modulators and fiber coupled telecom modulators.

16. The method according to claim 1 wherein said step of directing, focusing and combining is achieved using fiber optic components.

17. The method according to claim 1 wherein said at least one bulk non-linear optical crystal is selected from the group consisting of Potassium Titanyl Arsenate (KTA), Potassium Titanyl Phosphate (KTP), Rubidium Titanyl Phosphate (RTP), Rubidium Titanyl Arsenate (RTA), Lithium Niobate (LiNbO$_3$ or LNB), Lithium Tantalate (LiTaO$_3$ or LTA), MgO:LiNbO$_3$, Silver Thiogallate (AgGaS$_2$), Silver Selenogallate (AgGaSe$_2$), Gallium Selenide (GaSe), Mercury Thiogallate HgGa$_2$S$_4$ (HGS), Lithium Thioindate (LiInS$_2$) Lithium Selenoindate (LiInSe$_2$) and Zinc-Germanium Diphosphide (ZnGeP$_2$), etc.

18. The method according to claim 1 wherein at least one bulk non-linear optical crystal is a bulk KTA crystal cut at an angle for type IIa phase matching with $\theta\sim70°$ and $\phi\sim0°$ or $\theta\sim65°$ and $\phi\sim90°$ from the z-axis of the crystals, so as to reduce walk-off of said high energy pump pulses with wavelengths near 1.05 µm and said CW laser beam with wavelength near 1.6 µm, and wherein said bulk KTA crystal produces said mid-IR output pulses with wavelengths near 3 µm for high efficiency.

19. The method according to claim 1 wherein said at least one optical parametric amplifier includes a non-linear crystal waveguide.

20. The method according to claim 1 wherein step d) includes directing said high energy picosecond mid-IR pulses at wavelength $\lambda_3$ into a flexible waveguide capable of transporting said high energy picosecond mid-IR pulses at wavelength $\lambda_3$.

21. The method according to claim 1 wherein including a flexible wave guide containing gain medium for the high energy pump pulses and wherein high energy gain pulses are directed into said flexible wave guide and said optical parametric amplifiers are placed at an output of the flexible gain medium.

22. The method according to claim 21 wherein said flexible waveguide has a replaceable or removable tip at its output.

23. A laser system to produce high power mid-infrared (IR) laser pulses having a wavelengths $\lambda_3$ lying between 2 and 15 µm, comprising:
   a) a laser for producing high energy pump pulses with wavelength $\lambda_1$ between about 1.0 and about 1.1 µm, pulse duration between about 1 and about 1000 ps and high energy larger than about 10 µJ;
   b) a laser for producing lower power continuous wave (CW) laser beam having a power in a range between about 1 to about 100 mW, with a wavelength $\lambda_2$ satisfying a relation $1/\lambda_2 = 1/\lambda_1 - 1/\lambda_3$ wherein said wavelength $\lambda_2$ is between about 1 to about 2 µm;
   c) at least one optical parametric amplifier, each having at least one bulk non-linear optical crystal;
   d) means for directing, focusing and combining said high energy pump pulses and said CW laser beam such a way that they have substantial spatial and temporal overlap, and directing said combined high energy pump pulses and CW laser beam into said at least one optical parametric amplifier, said at least one optical parametric amplifier having at least one bulk non-linear optical crystal, without an optical parametric oscillator being present between the CW laser beam and said optical parametric amplifier, with the peak intensity of the high energy pump pulses sufficient such that high energy mid-IR pulses at wavelengths $\lambda_3$ between 2 and 15 µm are produced through three wave mixing between said spatially overlapped high energy pump pulses and CW laser beam in said at least one bulk non-linear crystal;
   e) means for shaping the spectral and temporal profile of said high energy mid-IR pulses either directly at said mid-IR wavelengths, or indirectly through the shaping of said CW laser beam before said at least one optical parametric amplifier; and
   f) means for transporting said high energy mid-IR pulses at wavelengths $\lambda_3$ from an output of said at least one optical parametric amplifier to a desired location.

24. The apparatus according to claim 23 wherein said low power laser for producing CW laser beam is a broadband diode laser.

25. The apparatus according to claim 23 wherein said laser for producing high energy pump pulses includes a picosecond mode-locked laser and an amplifier for amplifying an output of a picosecond mode-locked laser to an energy greater than 10 µJ.

26. The apparatus according to claim 25 wherein said high energy pump pulses are produced by amplifying the output of a picosecond mode-locked Yb doped fibre laser to an energy greater than 10 µJ, using a Yb doped fibre amplifier and the optional addition of a subsequent multi-pass diode pumped solid-state laser amplifier.

27. The apparatus according to claim 25 wherein the temporal overlap of said CW laser beam and said high energy pump pulses is stabilized by using cross-phase modulation with said said CW laser beam in said picosecond mode-locked laser.

28. The apparatus according to claim 23 wherein said at least one optical parametric amplifier is a cascade of optical parametric amplifiers, wherein an amplified field from one optical parametric amplifier becomes a pump field for at least one of the subsequent optical parametric amplifiers in said cascade, producing additional wavelengths $\lambda_4$ through $\lambda_n$, where n is determined by the number of cascaded optical parametric amplifiers.

29. The apparatus according to claim 23 wherein said at least one optical parametric amplifier is a first optical parametric amplifier and wherein said pump pulses have a $\lambda_1$ and said CW laser beam has a $\lambda_2$ such that said high energy mid-IR pulses have wavelength $\lambda_3$ between 2.8 and 3.1 µm corresponding to the OH-stretch absorption band of liquid water.

30. The apparatus according to claim 29 wherein said high energy broadband mid-IR pulses with wavelength $\lambda_3$ are further amplified in at least a second optical parametric amplifier in a cascade that uses as a pump the amplified output of said first optical parametric amplifier at said wavelength $\lambda_2$.

31. The apparatus according to claim 23 wherein said at least one optical parametric amplifier is a first optical parametric amplifier and wherein said pump pulses have a $\lambda_1$ and said CW laser beam has a $\lambda_2$ such that said high energy mid-IR pulses have a wavelength $\lambda_3$ between approximately 5.5 and 6.5 µm corresponding to amide absorption bands.

32. The apparatus according to claim 23 wherein a bandwidth of an output of at least one of an optical parametric amplifier is increased using a non-linear process.

33. The apparatus according to claim 23 including additional optical combining elements after which said laser beam with wavelength $\lambda_i$ is overlapped with one or several of said laser beams with wavelengths $\lambda_1, \lambda_2, \ldots, \lambda_n$ and used as a single laser beam thereafter.

34. The apparatus according to claim 23 wherein the energy of said high energy mid-IR pulses is adjusted by controlling an energy of said high energy pump pulses.

35. The apparatus according to claim 23 wherein said means for directing, focusing and combining includes fibre optic components.

36. The apparatus according to claim 23 wherein said at least one bulk non-linear optical crystal is selected from the group consisting of Potassium Titanyl Arsenate (KTA), Potassium Titanyl Phosphate (KTP), Rubidium Titanyl Phosphate (RTP), Rubidium Titanyl Arsenate (RTA), Lithium Niobate (LiNbO$_3$ or LNB), Lithium Tantalate (LiTaO$_3$ or LTA), MgO:LiNbO$_3$, Silver Thiogallate (AgGaS$_2$), Silver Selenogallate (AgGaSe$_2$), Gallium Selenide (GaSe), Mercury Thiogallate HgGa$_2$S$_4$ (HGS), Lithium Thioindate (LiInS$_2$) Lithium Selenoindate (LiInSe$_2$) and Zinc-Germanium Diphosphide (ZnGeP$_2$), etc.

37. The apparatus according to claim 23 wherein the bandwidth of at least one of said at least one optical parametric amplifier is increased through the use of a non-collinear phase matching geometry.

38. The apparatus according to claim 37 where said at least one optical parametric amplifier with non-collinear phase matching consists of a bulk KTA crystal cut at an angle for type IIb with $\theta \sim 45°$ and $\phi \sim 0°$ or $\theta \sim 35°$ and $\phi \sim 90°$ from the z-axis of the crystals, with non-collinear angle chosen to attain the desired amplified bandwidth when using said high energy pump pulses with wavelengths near 1.05 µm and said CW laser beam with wavelength near 1.6 µm thereby producing said high energy mid-IR output pulses with wavelengths near 3 µm.

39. The apparatus according to claim 37 wherein the output of said at least one optical parametric amplifier with a non-collinear phase matching geometry is amplified to higher energies in at least a second optical parametric amplifier with a collinear phase matching and a thickness that is thin enough to support the desired bandwidth, in order to produce said high energy mid-IR pulses as an idler beam with good spatial quality.

40. The apparatus according to claim 23 wherein the wavelength of said high energy mid-IR pulses is tuned by rotating said at least one bulk non-linear crystal.

41. The apparatus according to claim 23 wherein said at least one optical parametric amplifier includes a non-linear crystal waveguide.

42. The apparatus according to claim 23 wherein said spectral and temporal shaping shape said high energy mid-IR pulses to an approximately bandwidth limited time duration.

43. The apparatus according to claim 42 wherein a portion of said approximately bandwidth limited pulses are used to generate an optical continuum which is subsequently mixed with said approximately bandwidth limited pulses to generate high energy pulses at additional wavelengths.

44. The apparatus according to claim 23 wherein said transporting means includes a flexible fibre waveguide capable of transporting said high energy mid-IR pulses.

45. The apparatus according to any of claim 23 including a flexible wave guide containing gain medium for the said high energy pump pulses and wherein said at least one optical parametric amplifiers are placed at the output of the flexible gain medium.

46. The apparatus according to claim 23 wherein said transporting means includes a replaceable or removable tip at its output.

* * * * *

UNITED STATES PATENT AND TRADEMARK OFFICE
CERTIFICATE OF CORRECTION

PATENT NO. : 7,630,418 B2  Page 1 of 2
APPLICATION NO. : 11/328462
DATED : December 8, 2009
INVENTOR(S) : Franjic et al.

It is certified that error appears in the above-identified patent and that said Letters Patent is hereby corrected as shown below:

Col. 16, line 23, replace claim 23 with the following:

23. A laser system to produce high power mid-infrared (IR) laser pulses having a wavelengths $\lambda_3$ lying between 2 and 15 µm, comprising:

a) a laser for producing high energy pump pulses with wavelength $\lambda_1$ between about 1.0 and about 1.1 µm, pulse duration between about 1 and about 1000 ps and high energy larger than about 10 µJ;

b) a low power laser for producing low power continuous wave (CW) laser beam having a power in a range between about 1 to about 100mW, with a wavelength $\lambda_2$ satisfying a relation $1/\lambda_2 = 1/\lambda_1 - 1/\lambda_3$ wherein said wavelength $\lambda_2$ is between about 1.19 to about 2 µm;

c) at least one optical parametric amplifier, each having at least one bulk non-linear optical crystal;

d) means for directing, focusing and combining said high energy pump pulses and said CW laser beam in such a way that they have substantial spatial and temporal overlap, and directing said combined high energy pump pulses and CW laser beam into said at least one optical parametric amplifier, said at least one optical parametric amplifier having at least one bulk non-linear optical crystal, without an optical parametric oscillator being present between the CW laser beam and said optical parametric amplifier, with the peak intensity of the high energy pump pulses sufficient such that high energy mid-IR pulses at wavelengths $\lambda_3$ between 2 and 15 µm are produced through three wave mixing between said spatially overlapped high energy pump pulses and CW laser beam in said at least one bulk non-linear crystal;

Signed and Sealed this

Third Day of August, 2010

David J. Kappos
*Director of the United States Patent and Trademark Office* e) means for shaping the spectral and temporal profile of said high energy mid-IR pulses either directly at said mid-IR wavelengths, or indirectly through the shaping of said CW laser beam before said at least one optical parametric amplifier; and f) means for transporting said high energy mid-IR pulses at wavelengths $\lambda_3$ from an output of said at least one optical parametric amplifier to a desired location.

Col. 16, line 60, replace claim 24 with the following:

24. The apparatus according to claim 23 wherein said low power laser for producing said CW laser beam is a broadband diode laser.

Col. 17, line 27, replace claim 30 with the following:

30. The apparatus according to claim 29 wherein said high energy mid-IR pulses with wavelength $\lambda_3$ are further amplified in at least a second optical parametric amplifier in a cascade that uses as a pump the amplified output of said first optical parametric amplifier at said wavelength $\lambda_2$.